United States Patent
Hughes et al.

(10) Patent No.: US 10,954,215 B2
(45) Date of Patent: Mar. 23, 2021

(54) COMPOUNDS AS MODULATORS OF ROR GAMMA

(71) Applicant: Boehringer Ingelheim International GmbH, Ingelheim am Rhein (DE)

(72) Inventors: Robert Owen Hughes, Newtown, CT (US); Xiang Li, New Milford, CT (US); Peter Allen Nemoto, Southbury, CT (US); Lana Louise Smith Keenan, Ridgefield, CT (US); Lifen Wu, New Milford, CT (US); Zhaoming Xiong, Ridgefield, CT (US)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/469,075

(22) PCT Filed: Dec. 12, 2017

(86) PCT No.: PCT/US2017/065699
§ 371 (c)(1),
(2) Date: Jun. 12, 2019

(87) PCT Pub. No.: WO2018/111803
PCT Pub. Date: Jun. 21, 2018

(65) Prior Publication Data
US 2020/0071298 A1   Mar. 5, 2020

Related U.S. Application Data

(60) Provisional application No. 62/433,268, filed on Dec. 13, 2016.

(51) Int. Cl.
| | |
|---|---|
| C07D 401/14 | (2006.01) |
| A61P 37/02 | (2006.01) |
| C07D 207/16 | (2006.01) |
| C07D 401/04 | (2006.01) |
| C07D 401/10 | (2006.01) |
| C07D 401/12 | (2006.01) |
| C07D 403/04 | (2006.01) |
| C07D 409/04 | (2006.01) |
| C07D 413/04 | (2006.01) |
| C07D 417/04 | (2006.01) |
| C07D 491/107 | (2006.01) |

(52) U.S. Cl.
CPC .......... *C07D 401/14* (2013.01); *A61P 37/02* (2018.01); *C07D 207/16* (2013.01); *C07D 401/04* (2013.01); *C07D 401/10* (2013.01); *C07D 401/12* (2013.01); *C07D 403/04* (2013.01); *C07D 409/04* (2013.01); *C07D 413/04* (2013.01); *C07D 417/04* (2013.01); *C07D 491/107* (2013.01)

(58) Field of Classification Search
None
See application file for complete search history.

(56) References Cited

U.S. PATENT DOCUMENTS

2020/0024257 A1 * 1/2020 Duan ............... C07D 413/14

FOREIGN PATENT DOCUMENTS

| WO | 2007106705 A1 | 9/2007 |
|---|---|---|
| WO | 2012100732 A1 | 8/2012 |
| WO | 2013029338 A1 | 3/2013 |
| WO | 2013171729 A2 | 11/2013 |

OTHER PUBLICATIONS

Gege et al., "Retinoid-related orphan receptor gamma t (ROR[gamma]t) inhibitors from Vitae Pharmaceuticals (WO2015116904) and structure proposal for their Phase I candidate VTP-43742", Expert Opinion on Therapeutic Patents, Feb. 2016, vol. 26, No. 6, pp. 737-744.
International Search Repot and Written Opinion for corresponding application, PCT/US2017/065699, dated Mar. 6, 2018.
Ndagi et al., "Re-emergence of an orphan therapeutic target for the treatment of resistant prostate cancer—a thorough conformational and binding analysis for ROR-g protein", Journal of biomolecular structure & dynamics, 2018, vol. 36, No. 2, pp. 335-350.

* cited by examiner

*Primary Examiner* — Joseph R Kosack
(74) *Attorney, Agent, or Firm* — Philip I. Datlow

(57) ABSTRACT

The present invention encompasses compounds of the formula (I) wherein the variables are defined herein which are suitable for the modulation of RORγ and the treatment of diseases related to the modulation of RORγ. The present invention also encompasses processes of making compounds of formula (I) and pharmaceutical preparations containing them.

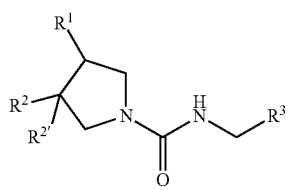

8 Claims, No Drawings

COMPOUNDS AS MODULATORS OF ROR GAMMA

FIELD OF THE INVENTION

The present invention relates to novel compounds which modulate the activity of RORγ and their use as medicaments.

BACKGROUND

RORγ (retinoic acid receptor related orphan receptor gamma) (also referred to as "RORγt") is a transcription factor belonging to the steroid hormone receptor superfamily (reviewed in Jetten 2006. Adv. Dev Biol. 16:313-355). RORγ has been identified as a transcriptional factor that is required for the differentiation of T cells and secretion of Interleukin 17 (IL-17) from a subset of T cells termed $Th_{17}$ cells (Ivanov, Cell 2006, 126, 1121-1133). The rationale for the use of a RORγ targeted therapy for the treatment of chronic inflammatory diseases is based on the emerging evidence that $Th_{17}$ cells and the cytokine IL-17 contribute to the initiation and progression of the pathogenesis of several autoimmune diseases including psoriasis, ankylosing spondylitis, rheumatoid arthritis, multiple sclerosis and Crohn's disease (reviewed in Miossec, Nature Drug Discovery 2012, 11, 763-776; see also Khan et al., Bioorganic & Medicinal Chemistry Letters 23 (2013), 532-536). The outcome of recent clinical trials with neutralizing antibodies to IL-17 and its receptor IL-17RA (Leonardi 2012, New England Journal of Medicine, 366, 1190-1199; Papp 2012, New England Journal of Medicine 366, 1181-1189) in psoriasis highlight the role of IL-17 in the pathogenesis of this disease. As such, attenuation of IL-17 secretion from activated $Th_{17}$ T cells via inhibition of RORγ may offer similar therapeutic benefit.

BRIEF SUMMARY OF THE INVENTION

The invention comprises a novel class of heteroaromatic compounds and methods for making and using the same, said compounds having the general structure of formula (I), wherein the substituent groups are as herein defined:

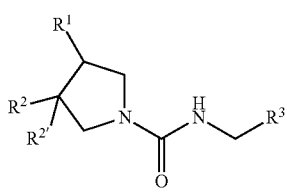

I

These compounds are useful for the treatment of autoimmune and allergic disorders in that they exhibit potent inhibitory activity against RORγ.

DETAILED DESCRIPTION OF THE INVENTION

In an embodiment of the invention, there are provided compounds of the formula I

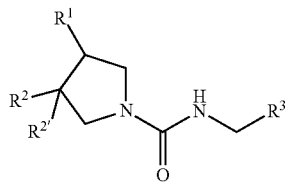

I wherein:

$R^{2'}$ is H; and $R^1$ and $R^2$ are independently selected from benzothiophen-3-yl, isoquinolinyl, [1,2,4]-oxadiazolyl, phenyl, pyrazolyl, pyridyl, thiazolyl, 1H-[1,2,4]triazolyl and 2H-[1,2,3]triazolyl;

or $R^2$ and $R^{2'}$ form a spiro benzofuran-3-one ring; and $R^1$ is selected from $C_{1-6}$alkyl, benzothiophen-3-yl, isoquinolinyl, [1,2,4]-oxadiazolyl, phenyl, pyrazolyl, pyridyl, thiazolyl, 1H-[1,2,4]triazolyl and 2H-[1,2,3]triazolyl;

wherein $R^1$ and $R^2$ are each optionally substituted by one to two groups independently selected from $C_{1-4}$alkyl, $C_{3-5}$cycloalkyl, cyclopropylmethyl, —$CF_3$, halogen, —$OCF_3$, —OH, —$OCH_3$ and phenyl;

$R^3$ is selected from phenyl, pyridyl and pyrimidinyl;

wherein $R^3$ is substituted with a group selected from —$SO_2C_{1-3}$alkyl and —$SO_2NHC_{1-3}$alkyl;

or an enantiomer or a salt thereof.

In another embodiment, there are provided compounds of the formula I as described according to the embodiment above and wherein $R^2$ is H; and $R^1$ and $R^2$ are independently selected from benzothiophen-3-yl, isoquinolin-5-yl, [1,2,4]-oxadiazol-5-yl, phenyl, 4- and 5-pyrazolyl, 2- and 3-pyridyl, thiazol-2-yl, 1H-[1,2,4]triazol-5-yl and 2H-[1,2,3]triazol-5-yl;

or $R^2$ and $R^{2'}$ may form a spiro benzofuran-3-one ring; and $R^1$ is selected from isopropyl, benzothiophen-3-yl, isoquinolin-5-yl, [1,2,4]-oxadiazol-5-yl, phenyl, 4- and 5-pyrazolyl, 2- and 3-pyridyl, thiazol-2-yl, 1H-[1,2,4]triazol-5-yl and 2H-[1,2,3]triazol-5-yl;

$R^1$ and $R^2$ are each optionally substituted by one to two groups independently selected from $C_{1-4}$alkyl, $C_{3-5}$cycloalkyl, cyclopropylmethyl, —$CF_3$, Cl, —$OCF_3$, —OH, —$OCH_3$ and phenyl;

$R^3$ is selected from phenyl, 2- and 3-pyridyl and 2-pyrimidinyl;

wherein $R^3$ is substituted with a group selected from —$SO_2CH_2CH_3$ and —$SO_2NHCH_3$;

or an enantiomer or a salt thereof.

In another embodiment, there are provided compounds of the formula I as described according to the embodiment above and wherein R$^{2'}$ is H; and R$^1$ and R$^2$ are independently selected from benzothiophen-3-yl, isoquinolin-5-yl, phenyl, 4- and 5-pyrazolyl, 2-pyridyl and 1H-[1,2,4]triazol-5-yl;

or

R$^2$ and R$^{2'}$ may form a spiro benzofuran-3-one ring; and

R$^1$ is selected from isopropyl, benzothiophen-3-yl, isoquinolin-5-yl, phenyl, 4- and 5-pyrazolyl, 2-pyridyl and 1H-[1,2,4]triazol-5-yl;

wherein R$^1$ and R$^2$ are each optionally substituted by one to two groups independently selected from C$_{1-4}$alkyl, C$_{3-5}$cycloalkyl, cyclopropylmethyl, —CF$_3$, Cl, —OCF$_3$, —OH and —OCH$_3$;

R$^3$ is selected from phenyl and 2-pyridyl;

wherein R$^3$ is substituted with a group selected from —SO$_2$CH$_2$CH$_3$ and —SO$_2$NHCH$_3$;

or an enantiomer or a salt thereof.

In another embodiment, there are provided compounds of the formula I as described according to the embodiment above and wherein R$^{2'}$ is H; and R$^1$ and R$^2$ are independently selected from isopropyl, phenyl, 4- and 5-pyrazolyl and 2-pyridyl;

or

R$^2$ and R$^{2'}$ may form a spiro benzofuran-3-one ring; and

R$^1$ is selected from isopropyl and phenyl;

wherein R$^1$ and R$^2$ are each optionally substituted by one to two groups independently selected from methyl, isopropyl, tert-butyl, cyclopropyl, cyclopentyl, —CF$_3$, Cl and —OCF$_3$;

R$^3$ is selected from phenyl and 2-pyridyl;

wherein R$^3$ is substituted with a group selected from —SO$_2$CH$_2$CH$_3$ and —SO$_2$NHCH$_3$; or an enantiomer or a salt thereof.

In another aspect of the invention, there is provided a compound of the general formula I according to any of the embodiments above, or a pharmaceutically acceptable salt thereof for use in a therapeutic method as described hereinbefore and hereinafter Table 1 shows representative compounds of the invention which can be made by the methods described in the general synthetic schemes, the examples, and known methods in the art.

TABLE 1

| Cpd No. | Structure |
|---|---|
| 1 | |
| 2 | |
| 3 | 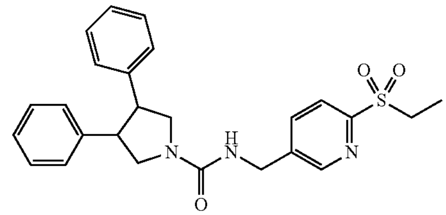 [SMILES: CCS(=O)(=O)c1ccc(CNC(=O)N2CC(c3ccccc3)C(c3ccccc3)C2)cn1] |
| 4 | 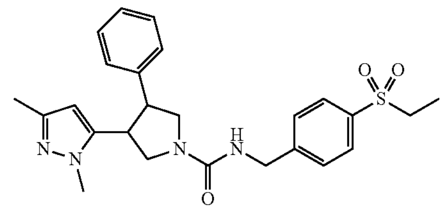 [SMILES: CCS(=O)(=O)c1ccc(CNC(=O)N2CC(c3ccccc3)C(c3cc(C)nn3C)C2)cc1] |
| 5 | 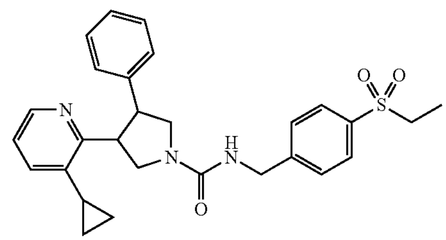 [SMILES: CCS(=O)(=O)c1ccc(CNC(=O)N2CC(c3ccccc3)C(c3ncccc3C3CC3)C2)cc1] |
| 6 | 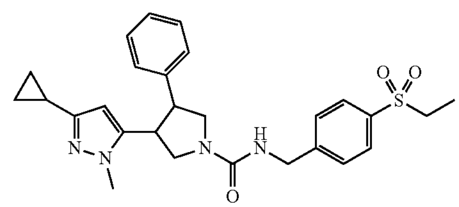 [SMILES: CCS(=O)(=O)c1ccc(CNC(=O)N2CC(c3ccccc3)C(c3cc(C4CC4)nn3C)C2)cc1] |
| 7 | 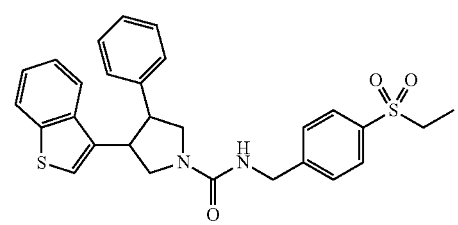 [SMILES: CCS(=O)(=O)c1ccc(CNC(=O)N2CC(c3ccccc3)C(c3csc4ccccc34)C2)cc1] |
| 8 | 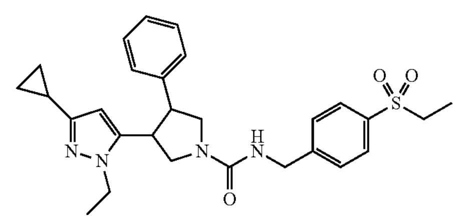 [SMILES: CCn1nc(C2CC2)cc1C1CN(C(=O)NCc2ccc(S(=O)(=O)CC)cc2)CC1c1ccccc1] |

TABLE 1-continued

| Cpd No. | Structure |
|---|---|
| 9 | |
| 10 | |
| 11 | |
| 12 | |
| 13 | |
| 14 | |
| 15 | 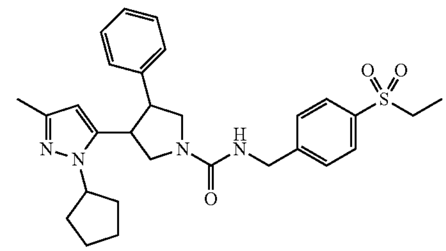 [SMILES: CCS(=O)(=O)c1ccc(CNC(=O)N2CC(c3ccccc3)C(c3cc(C)nn3C3CCCC3)C2)cc1] |
| 16A | 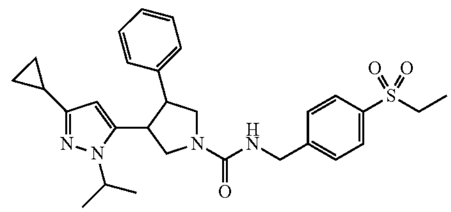 [SMILES: CCS(=O)(=O)c1ccc(CNC(=O)N2CC(c3ccccc3)C(c3cc(C4CC4)nn3C(C)C)C2)cc1] |
| 16B | 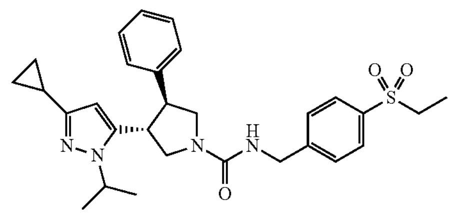 [SMILES: CCS(=O)(=O)c1ccc(CNC(=O)N2C[C@H](c3ccccc3)[C@@H](c3cc(C4CC4)nn3C(C)C)C2)cc1] |
| 16C | 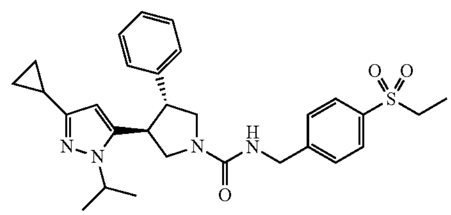 [SMILES: CCS(=O)(=O)c1ccc(CNC(=O)N2C[C@@H](c3ccccc3)[C@H](c3cc(C4CC4)nn3C(C)C)C2)cc1] |
| 17 | 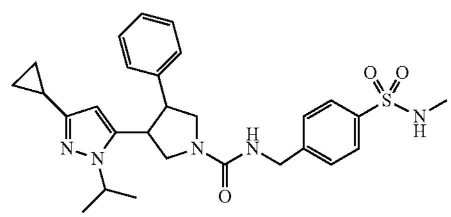 [SMILES: CNS(=O)(=O)c1ccc(CNC(=O)N2CC(c3ccccc3)C(c3cc(C4CC4)nn3C(C)C)C2)cc1] |
| 18 | 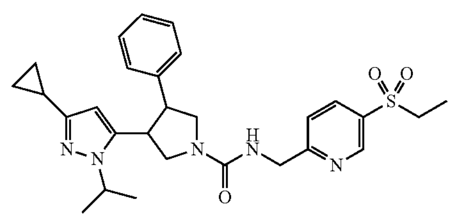 [SMILES: CCS(=O)(=O)c1ccc(CNC(=O)N2CC(c3ccccc3)C(c3cc(C4CC4)nn3C(C)C)C2)nc1] |
| 19 | 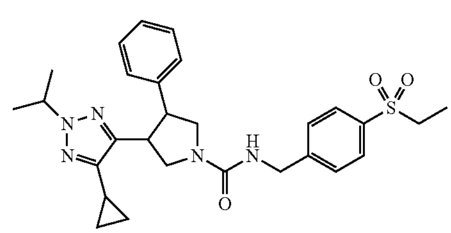 [SMILES: CCS(=O)(=O)c1ccc(CNC(=O)N2CC(c3ccccc3)C(c3nn(C(C)C)nc3C3CC3)C2)cc1] |

TABLE 1-continued

| Cpd No. | Structure |
|---|---|
| 20 | 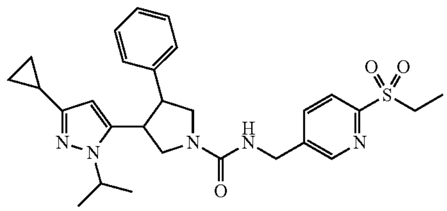 [SMILES: CCS(=O)(=O)c1ccc(CNC(=O)N2CC(c3ccccc3)C(c3cc(C4CC4)nn3C(C)C)C2)cn1] |
| 21 | 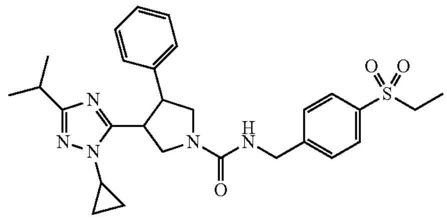 [SMILES: CCS(=O)(=O)c1ccc(CNC(=O)N2CC(c3ccccc3)C(c3nc(C(C)C)nn3C3CC3)C2)cc1] |
| 22 | 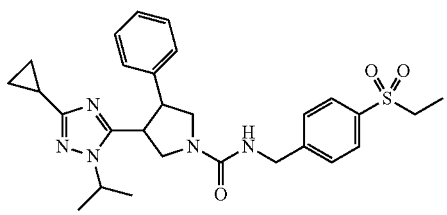 [SMILES: CCS(=O)(=O)c1ccc(CNC(=O)N2CC(c3ccccc3)C(c3nc(C4CC4)nn3C(C)C)C2)cc1] |
| 23 | 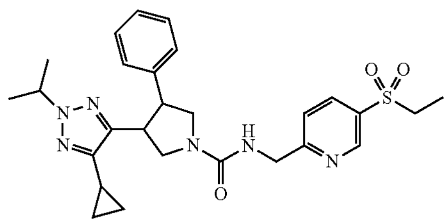 [SMILES: CCS(=O)(=O)c1ccc(CNC(=O)N2CC(c3ccccc3)C(c3nn(C(C)C)nc3C3CC3)C2)nc1] |
| 24 | 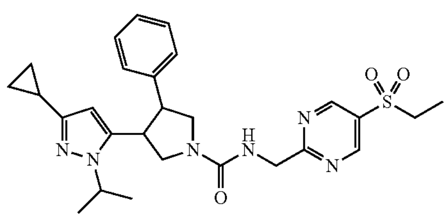 [SMILES: CCS(=O)(=O)c1cnc(CNC(=O)N2CC(c3ccccc3)C(c3cc(C4CC4)nn3C(C)C)C2)nc1] |
| 25 | 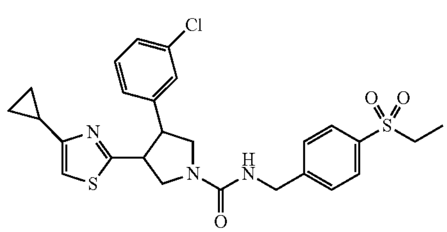 [SMILES: CCS(=O)(=O)c1ccc(CNC(=O)N2CC(c3cccc(Cl)c3)C(c3nc(C4CC4)cs3)C2)cc1] |
| 26 | 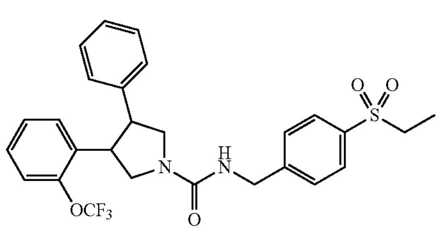 [SMILES: CCS(=O)(=O)c1ccc(CNC(=O)N2CC(c3ccccc3)C(c3ccccc3OC(F)(F)F)C2)cc1] |
| 27 | |
| 28 | |
| 29 | |
| 30 | |
| 31 | |
| 32 | |

TABLE 1-continued

| Cpd No. | Structure |
|---|---|
| 33 | 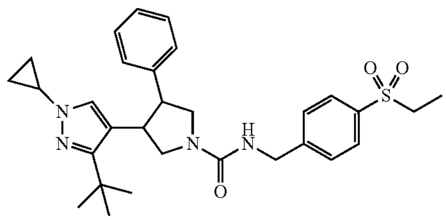 [SMILES: CCS(=O)(=O)c1ccc(CNC(=O)N2CC(c3ccccc3)C(c3cn(C4CC4)nc3C(C)(C)C)C2)cc1] |
| 34 | 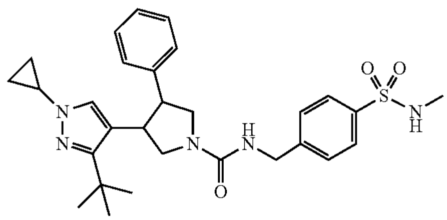 [SMILES: CNS(=O)(=O)c1ccc(CNC(=O)N2CC(c3ccccc3)C(c3cn(C4CC4)nc3C(C)(C)C)C2)cc1] |
| 35 | 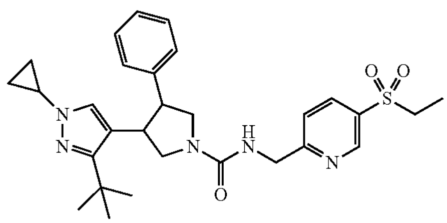 [SMILES: CCS(=O)(=O)c1ccc(CNC(=O)N2CC(c3ccccc3)C(c3cn(C4CC4)nc3C(C)(C)C)C2)nc1] |
| 36 | 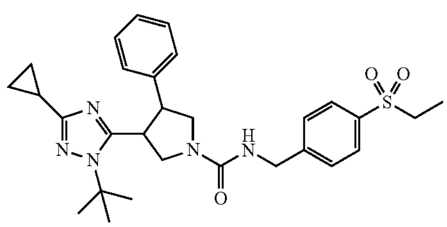 [SMILES: CCS(=O)(=O)c1ccc(CNC(=O)N2CC(c3ccccc3)C(c3nc(C4CC4)nn3C(C)(C)C)C2)cc1] |
| 37 | 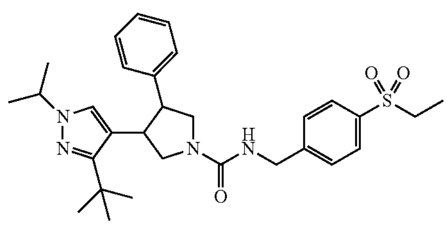 [SMILES: CCS(=O)(=O)c1ccc(CNC(=O)N2CC(c3ccccc3)C(c3cn(C(C)C)nc3C(C)(C)C)C2)cc1] |
| 38 | 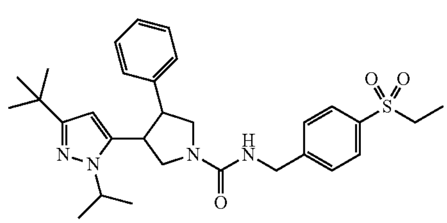 [SMILES: CCS(=O)(=O)c1ccc(CNC(=O)N2CC(c3ccccc3)C(c3cc(C(C)(C)C)nn3C(C)C)C2)cc1] |
| 39 | 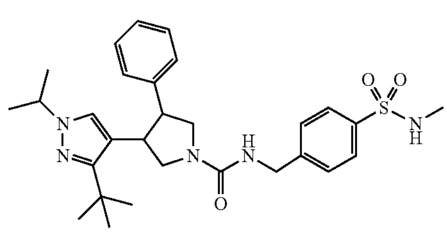 [SMILES: CNS(=O)(=O)c1ccc(CNC(=O)N2CC(c3ccccc3)C(c3cn(C(C)C)nc3C(C)(C)C)C2)cc1] |
| 40 | |
| 41 | |
| 42 | |
| 43 | |
| 44 | |
| 45 | |

TABLE 1-continued

| Cpd No. | Structure |
|---|---|
| 46 | (structure) |
| 47 | (structure) |
| 48 | (structure) |
| 49 | (structure) |
| 50 | (structure) |
| 51 | (structure) |
| 52 | (structure) |
| 53 | (structure) |
| 54 | (structure) |
| 55 | (structure) |
| 56 | (structure) |
| 57 | (structure) |

In one embodiment, the invention relates to compounds 1-57 depicted in Table 1 above, the enantiomers thereof and the pharmaceutically acceptable salts thereof.

Unless specifically indicated, throughout the specification and the appended claims, a given chemical formula or name shall encompass tautomers and all stereo, optical and geometrical isomers (e.g. enantiomers, diastereomers, E/Z isomers, etc.) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound. Some of the compounds of formula (I) can exist in more than one tautomeric form. The invention includes methods for using all such tautomers.

Compounds of the invention also include their isotopically-labelled forms. An isotopically-labelled form of an active agent of a combination of the present invention is identical to said active agent but for the fact that one or more atoms of said active agent have been replaced by an atom or atoms having an atomic mass or mass number different from the atomic mass or mass number of said atom which is usually found in nature. Examples of isotopes which are readily available commercially and which can be incorporated into an active agent of a combination of the present invention in accordance with well established procedures, include isotopes of hydrogen, carbon, nitrogen, oxygen, phosphorous, fluorine and chlorine, e.g., $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively. An active agent of a combination of the present invention, a prodrug thereof, or a pharmaceutically acceptable salt of either which contains one or more of the above-mentioned isotopes and/or other isotopes of other atoms is contemplated to be within the scope of the present invention.

The invention includes pharmaceutically acceptable derivatives of compounds of formula (I). A "pharmaceutically acceptable derivative" refers to any pharmaceutically acceptable salt or ester, or any other compound which, upon administration to a patient, is capable of providing (directly or indirectly) a compound useful for the invention, or a pharmacologically active metabolite or pharmacologically active residue thereof. A pharmacologically active metabolite shall be understood to mean any compound of the invention capable of being metabolized enzymatically or chemically. This includes, for example, hydroxylated or oxidized derivative compounds of the formula (I).

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates, subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminium, calcium, lithium, magnesium, potassium, sodium, zinc and the like. (also see Pharmaceutical salts, Berge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

In addition, within the scope of the invention is use of prodrugs of compounds of the formula (I). Prodrugs include those compounds that, upon simple chemical transformation, are modified to produce compounds of the invention. Simple chemical transformations include hydrolysis, oxidation and reduction. Specifically, when a prodrug is administered to a patient, the prodrug may be transformed into a compound disclosed hereinabove, thereby imparting the desired pharmacological effect.

The compounds of the invention are only those which are contemplated to be 'chemically stable' as will be appreciated by those skilled in the art. For example, peroxides or a compound which would have a 'dangling valency', or a 'carbanion' are not compounds contemplated by the inventive methods disclosed herein.

For all compounds disclosed hereinabove in this application, in the event the nomenclature is in conflict with the structure, it shall be understood that the compound is defined by the structure. All terms as used herein in this specification, unless otherwise stated, shall be understood in their ordinary meaning as known in the art. For example, "$C_{1-4}$alkyl" is a saturated aliphatic hydrocarbon monovalent radical containing 1-4 carbons such as methyl, ethyl, n-propyl, 1-methylethyl (isopropyl), n-butyl or t-butyl; "$C_{1-4}$ alkoxy" is a $C_{1-4}$ alkyl with a terminal oxygen, such as methoxy, ethoxy, propoxy, butoxy. All alkyl, alkenyl and alkynyl groups shall be understood as being branched or unbranched, cyclized or uncyclized where structurally possible and unless otherwise specified. Other more specific definitions are as follows:

The term "$C_{1-n}$-alkyl", wherein n is an integer from 2 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer 1 to n, either alone or in combination with another radical, denotes an acyclic, straight or branched chain divalent alkyl radical containing from 1 to n carbon atoms. For example the term C$_{1-4}$-alkylene includes —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$—CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_2$CH$_3$))—, —(CHCH(CH$_3$)$_2$)— and —C(CH$_3$)(CH$_2$CH$_3$)—.

The term "C$_{3-n}$-cycloalkyl", wherein n is an integer 3 to n, either alone or in combination with another radical denotes a cyclic, saturated, unbranched hydrocarbon radical with 3 to n C atoms. For example the term C$_{3-7}$-cycloalkyl includes cyclopropyl, cyclobutyl, cyclopentyl, cyclohexyl and cycloheptyl.

The term "heteroatom" as used herein shall be understood to mean atoms other than carbon such as O, N, S and P.

In all alkyl groups or carbon chains one or more carbon atoms can be optionally replaced by heteroatoms: O, S or N, it shall be understood that if N is not substituted then it is NH, it shall also be understood that the heteroatoms may replace either terminal carbon atoms or internal carbon atoms within a branched or unbranched carbon chain. Such groups can be substituted as herein above described by groups such as oxo to result in definitions such as but not limited to: alkoxycarbonyl, acyl, amido and thioxo.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl.

The term "heteroaryl" means an aromatic 5 to 6-membered monocyclic heteroaryl or an aromatic 7 to 11-membered heteroaryl bicyclic ring where at least one of the rings is aromatic, wherein the heteroaryl ring contains 1-4 heteroatoms such as N, O and S. Non-limiting examples of 5 to 6-membered monocyclic heteroaryl rings include furanyl, oxazolyl, isoxazolyl, oxadiazolyl, thiazolyl, pyrazolyl, pyrrolyl, imidazolyl, tetrazolyl, triazolyl, thienyl, thiadiazolyl, pyridinyl, pyrimidinyl, pyridazinyl, pyrazinyl, triazinyl, and purinyl. Non-limiting examples of 7 to 11-membered heteroaryl bicyclic heteroaryl rings include benzimidazolyl, quinolinyl, dihydro-2H-quinolinyl, tetrahydroquinolinyl, isoquinolinyl, quinazolinyl, indazolyl, thieno[2,3-d]pyrimidinyl, indolyl, isoindolyl, benzofuranyl, dihydrobenzofuranyl, benzopyranyl, benzodioxolyl, benzoxazolyl and benzothiazolyl.

The term "heterocyclyl" means a stable nonaromatic 4-8 membered monocyclic heterocyclic radical or a stable nonaromatic 6 to 11-membered fused bicyclic, bridged bicyclic or spirocyclic heterocyclic radical. The 5 to 11-membered heterocycle consists of carbon atoms and one or more, preferably from one to four heteroatoms chosen from nitrogen, oxygen and sulfur. The heterocycle may be either saturated or partially unsaturated. Non-limiting examples of nonaromatic 4-8 membered monocyclic heterocyclic radicals include tetrahydrofuranyl, azetidinyl, pyrrolidinyl, pyranyl, tetrahydropyranyl, dioxanyl, thiomorpholinyl, 1,1-dioxo-1$\lambda^6$-thiomorpholinyl, morpholinyl, piperidinyl, piperazinyl, and azepinyl. Non-limiting examples of nonaromatic 6 to 11-membered fused bicyclic radicals include octahydroindolyl, octahydrobenzofuranyl, and octahydrobenzothiophenyl. Non-limiting examples of nonaromatic 6 to 11-membered bridged bicyclic radicals include 2-azabicyclo[2.2.1]heptanyl, 3-azabicyclo[3.1.0]hexanyl, and 3-azabicyclo[3.2.1]octanyl. Non-limiting examples of nonaromatic 6 to 11-membered spirocyclic heterocyclic radicals include 7-aza-spiro[3,3]heptanyl, 7-spiro[3,4]octanyl, and 7-aza-spiro[3,4]octanyl. The term "heterocyclyl" or is intended to include all the possible isomeric forms.

The term "halogen" as used in the present specification shall be understood to mean bromine, chlorine, fluorine or iodine. The definitions "halogenated", "partially or fully halogenated"; partially or fully fluorinated; "substituted by one or more halogen atoms", includes for example, mono, di or tri halo derivatives on one or more carbon atoms. For alkyl, non-limiting examples would be —CH$_2$CHF$_2$, —CF$_3$ etc.

Each alkyl, cycloalkyl, heterocycle, aryl or heteroaryl, or the analogs thereof, described herein shall be understood to be optionally partially or fully halogenated.

As used herein, "nitrogen" or N and "sulfur" or S includes any oxidized form of nitrogen and sulfur and the quaternized form of any basic nitrogen. For example, for an —S—C$_{1-6}$ alkyl radical, unless otherwise specified, this shall be understood to include —S(O)—C$_{1-6}$ alkyl and —S(O)$_2$—C$_{1-6}$ alkyl, likewise, —S—R$_a$ may be represented as phenyl-S(O)$_m$— when R$_a$ is phenyl and where m is 0, 1 or 2.

General Synthetic Methods

The compounds of the invention may be prepared by the methods and examples presented below and methods known to those of ordinary skill in the art. The methods that are described here are intended as an illustration and for the enablement of the instant invention without restricting the scope of its subject matter, the claimed compounds, and the examples. In the methods of synthesis and examples described hereinafter, the substituents R$^1$, R$^2$, R$^3$, R$^4$, R$^5$, X, Y and A shall have the meanings defined hereinbefore in the detailed description of the compounds of formula I. Optimum reaction conditions and reaction times may vary depending on the particular reactants used. Unless otherwise specified, solvents, temperatures, pressures, and other reaction conditions may be readily selected by one of ordinary skill in the art. Specific procedures are provided below. Intermediates used in the syntheses below are either commercially available or easily prepared by methods known to those skilled in the art. Reaction progress may be monitored by conventional methods such as thin layer chromatography (TLC) or high pressure liquid chromatography-mass spec (HPLC-MS). Intermediates and products may be purified by methods known in the art, including column chromatography, HPLC, preparative TLC or recrystallization. Discrete enantiomers may be obtained by resolution of racemic products using chiral HPLC.

List of abbreviations used in synthetic examples:

| | |
|---|---|
| Ac | Acetyl |
| ACN | Acetonitrile |
| AcOH | Acetic acid |
| aq | Aqueous |
| Bu | Butyl |
| Boc$_2$O | Di-tert-butyl dicarbonate |
| DCM | Dichloromethane |
| DIEA | N,N-diisopropylethylamine |
| DMAP | 4-Dimethylaminopyridine |
| DMF | N,N-Dimethylformamide |
| dppf | 1.1'-bis(diphenylphosphino)ferrocene |

| | |
|---|---|
| ES+ | Electron spray positive ionization |
| Et | Ethyl |
| EtOAc | Ethyl acetate |
| EtOH | Ethanol |
| h | hour(s) |
| HPLC | High performance liquid chromatography |
| i | Iso |
| LC | Liquid chromatography |
| Me | Methyl |
| MeOH | Methanol |
| min | Minutes |
| MS | Mass spectrometry |
| NMP | N-Methylpyrrolidinone |
| Pd/C | Palladium on carbon |
| Ph | Phenyl |
| PPh3 | Triphenylphosphine |
| Pr | Propyl |
| RaNi | Raney Nickel |
| RT | Retention time (HPLC) |
| rt | Ambient temperature |
| SFC | Supercritical Fluid Chromatography |
| t | Tertiary |
| tert | Tertiary |
| Tf | Triflate |
| TEA | Triethylamine |
| TFA | Trifluoroacetic acid |
| THF | Tetrahydrofuran |
| UPLC | Ultra Performance Liquid Chromatography |

Synthetic Examples

The general synthetic routes for the examples are outlined below. Most of the examples were synthesized by general route 1 with the substituted pyrrolidines as the key intermediates. The majority of the pyrrolidine intermediates were prepared from olefins via two types of 3+2 cycloadditions followed by the deprotection of benzyl or methyl groups, respectively. The substituted pyrrolidines react with carbamates to form the ureas as the final products in most of cases while some examples require further transformation after this step. For a set of triazole analogues, the triazole formation was conducted after urea formation in order to do synthesis in a parallel fashion as shown in the general synthetic route 2.

General synthetic route 1:

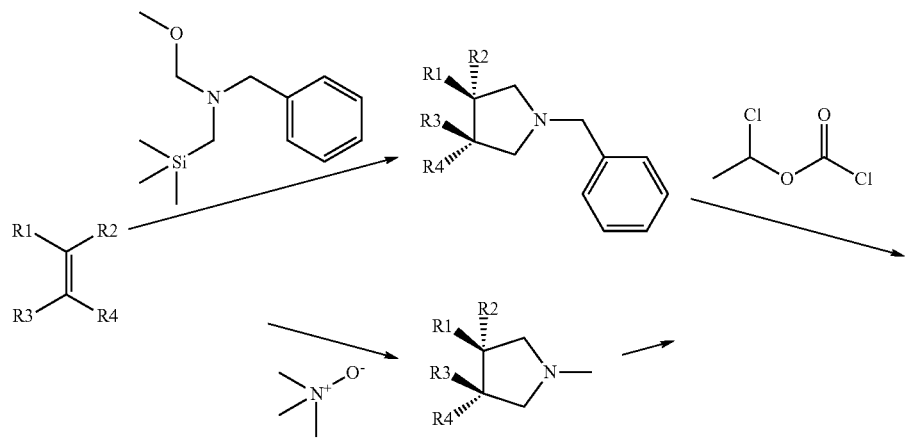

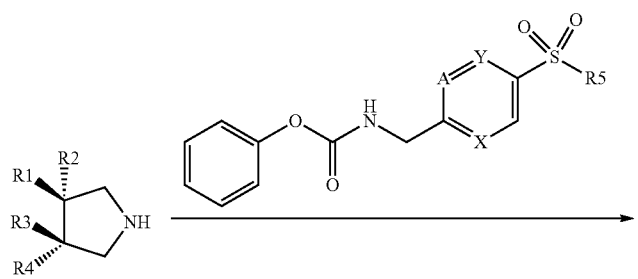

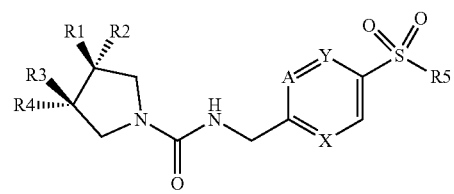

General synthetic route 2:

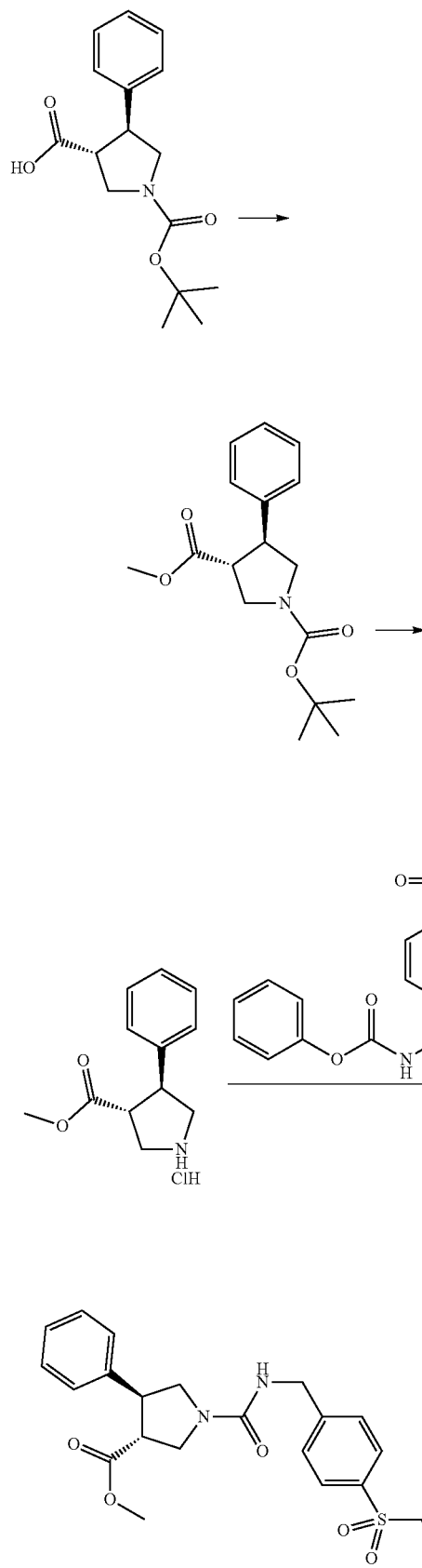

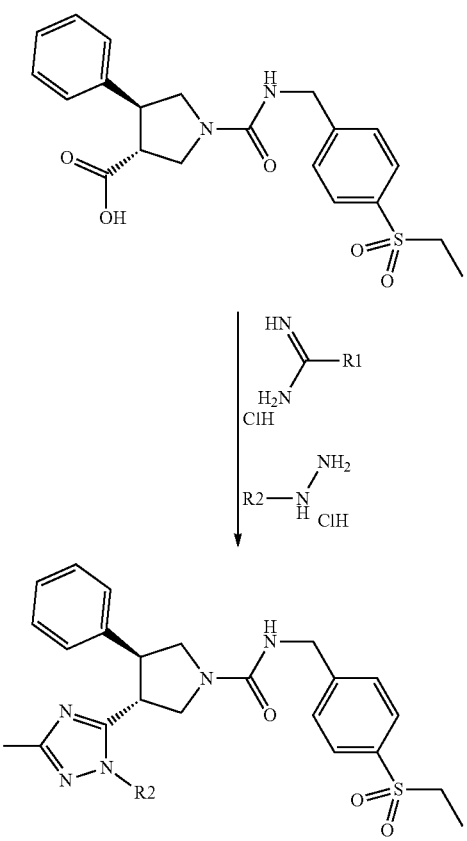

Method 1: Synthesis of Intermediate A

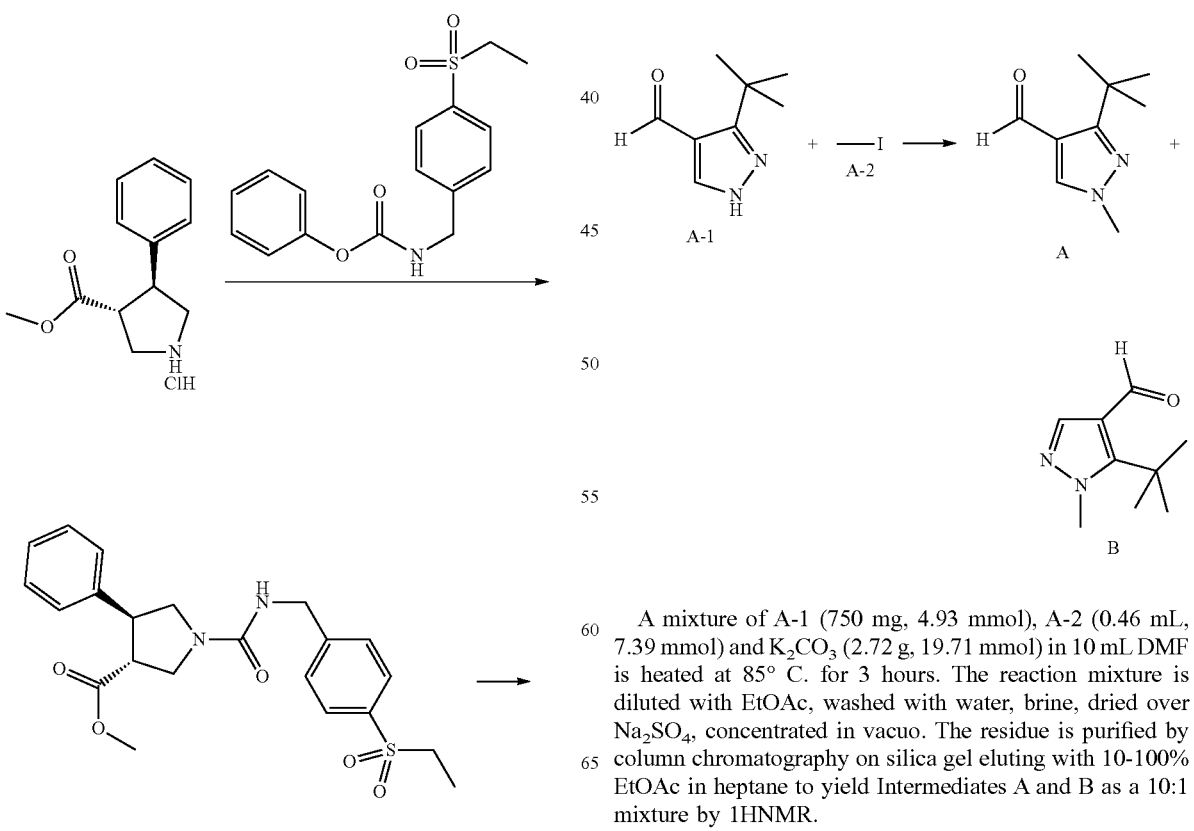

A mixture of A-1 (750 mg, 4.93 mmol), A-2 (0.46 mL, 7.39 mmol) and K$_2$CO$_3$ (2.72 g, 19.71 mmol) in 10 mL DMF is heated at 85° C. for 3 hours. The reaction mixture is diluted with EtOAc, washed with water, brine, dried over Na$_2$SO$_4$, concentrated in vacuo. The residue is purified by column chromatography on silica gel eluting with 10-100% EtOAc in heptane to yield Intermediates A and B as a 10:1 mixture by 1HNMR.

The following intermediate is prepared in a similar fashion:

| Intermediate | Structure |
|---|---|
| C | 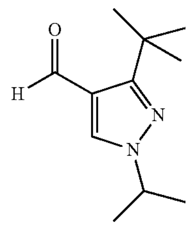 |
| H | |

Method 2: Synthesis of Intermediate D

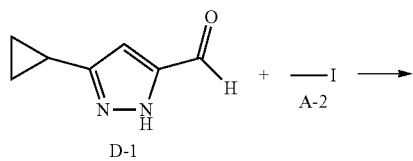

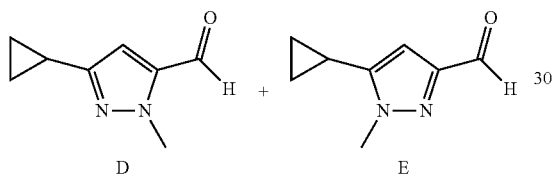

To a suspension of D-1 (500 mg, 3.67 mmol) in DMF (10 mL) is added A-2 (1.14 mL, 18.36 mmol) and K₂CO₃ (2.538 g, 18.36 mmol). The reaction mixture is heated at 80° C. overnight. The reaction mixture is diluted with EtOAc, washed with water, brine, dried over Na₂SO₄, concentrated in vacuo. The residue is purified by column chromatography on silica gel eluting with EtOAc in heptane to yield Intermediates D and E.

The following intermediates are prepared in similar fashion:

| Intermediate | Structure |
|---|---|
| F | 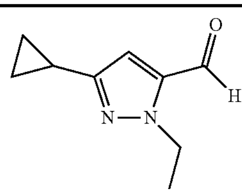 |
| G | 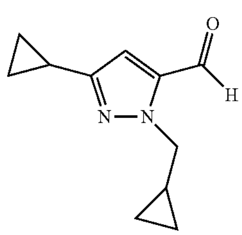 [SMILES: O=Cc1cc(C2CC2)nn1CC1CC1] |

Method 3: Synthesis of Intermediate I

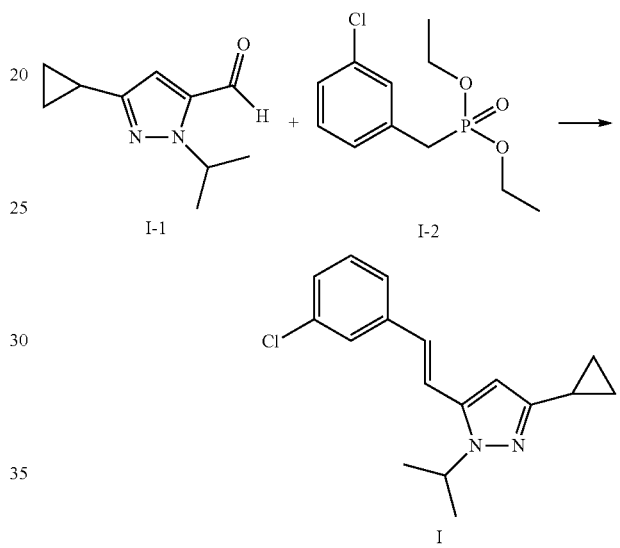

To a solution of I-1 (500 mg, 2.81 mmol) and I-2 (0.62 mL, 2.81 mmol) in THF (10 mL) in a water bath is added dropwise t-BuOK (1M in THF, 6.73 mL, 6.73 mmol). The reaction mixture is stirred at room temperature for 2 hours. The reaction mixture is quenched with water and extracted with EtOAc twice. The organics are combined and washed with brine, dried over Na₂SO₄, filtered and concentrated. The residue is purified by column chromatography on silica gel eluting with EtOAc in heptane to yield Intermediate I.

The following intermediates are prepared in similar fashion:

| Intermediate | Structure |
|---|---|
| J | 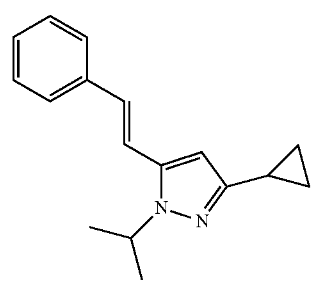 [SMILES: CC(C)n1nc(C2CC2)cc1/C=C/c1ccccc1] |

| Intermediate | Structure |
|---|---|
| K | (styryl-pyrazole with N-CH2-cyclopropyl and 3-cyclopropyl) |
| L | (styryl at pyrazole 4-position, 3-tert-butyl, N-methyl) |
| M | (styryl-pyrazole, 3-tert-butyl, N-isopropyl) |
| N | (styryl at 4-position, 3-tert-butyl, NH-pyrazole) |
| O | (styryl at 4-position, 3-tert-butyl, N-isopropyl) |
| P | (styryl-pyrazole, 3-methyl, N-cyclopentyl) |
| Q | (styryl-pyrazole, 3-methyl, N-methyl) |
| R | (styryl-pyrazole, 3-cyclopropyl, N-ethyl) |
| S | (styryl-pyrazole, 3-cyclopropyl, N-methyl) |
| T | (styryl-benzothiophene) |
| U | (2-cyclopropyl-6-[styryl-pyrazole]pyridine, N-isopropyl, 3-cyclopropyl) |

-continued
| Intermediate | Structure |
|---|---|
| V | 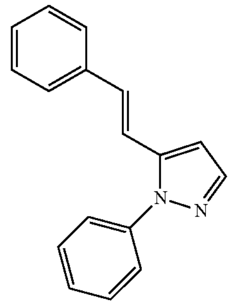 [SMILES: C(=C\c1ccnn1-c1ccccc1)/c1ccccc1] |
| W | 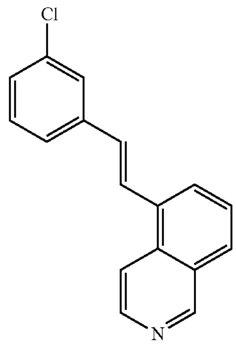 [SMILES: Clc1cccc(/C=C/c2cccc3cnccc23)c1] |
| X | 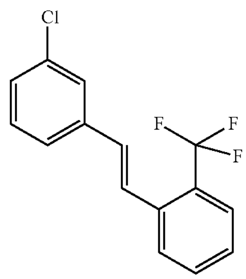 [SMILES: FC(F)(F)c1ccccc1/C=C/c1cccc(Cl)c1] |
| Y | 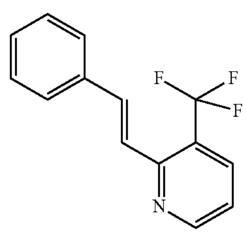 [SMILES: FC(F)(F)c1cccnc1/C=C/c1ccccc1] |
| Z | 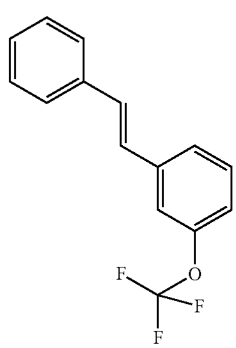 [SMILES: FC(F)(F)Oc1cccc(/C=C/c2ccccc2)c1] |
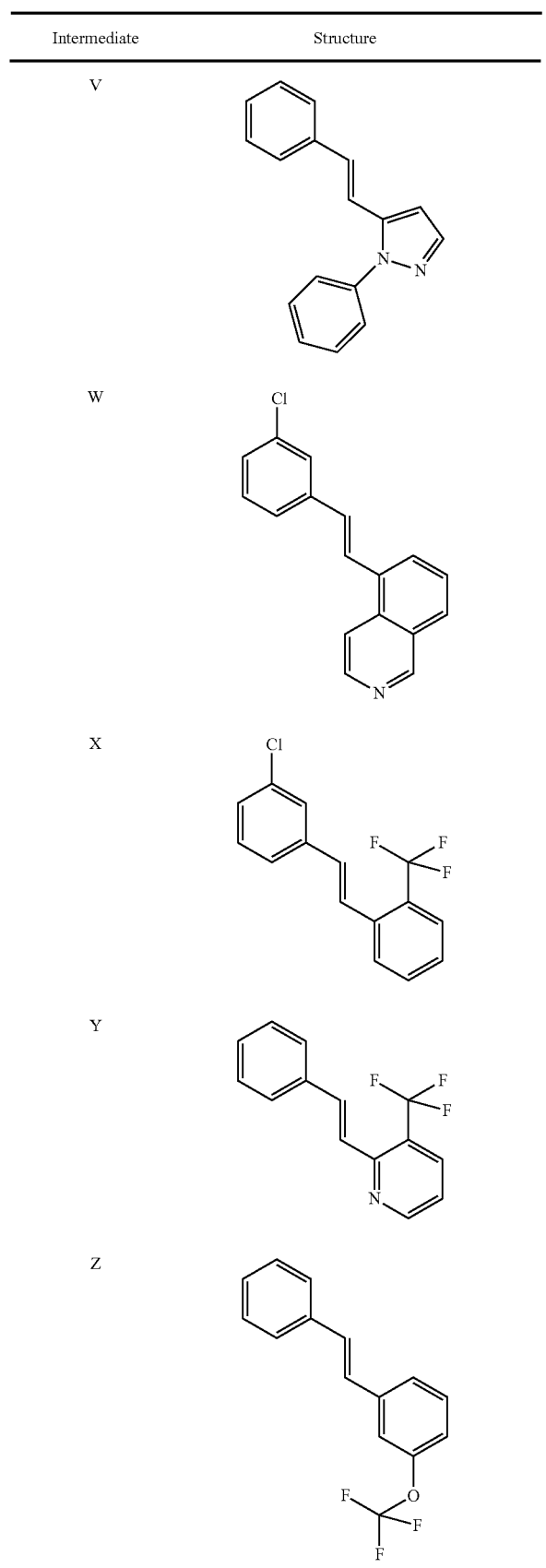
-continued
| Intermediate | Structure |
|---|---|
| AA | 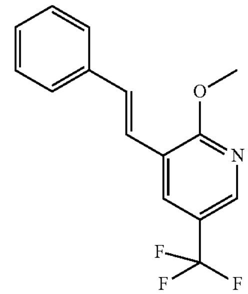 [SMILES: COc1ncc(C(F)(F)F)cc1/C=C/c1ccccc1] |
| BB | 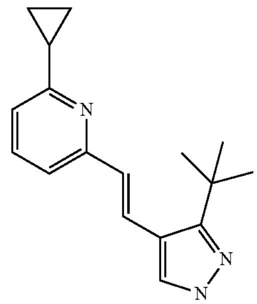 [SMILES: CC(C)(C)c1n[nH]cc1/C=C/c1cccc(C2CC2)n1] |
| CC | 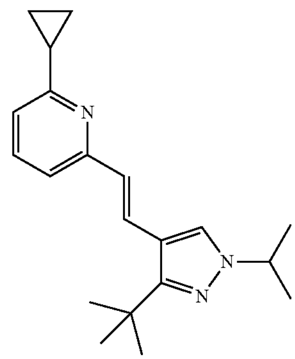 [SMILES: CC(C)n1cc(/C=C/c2cccc(C3CC3)n2)c(C(C)(C)C)n1] |
| DD | 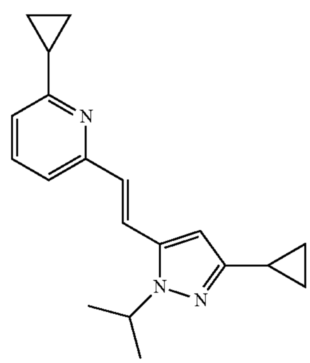 [SMILES: CC(C)n1nc(C2CC2)cc1/C=C/c1cccc(C2CC2)n1] |
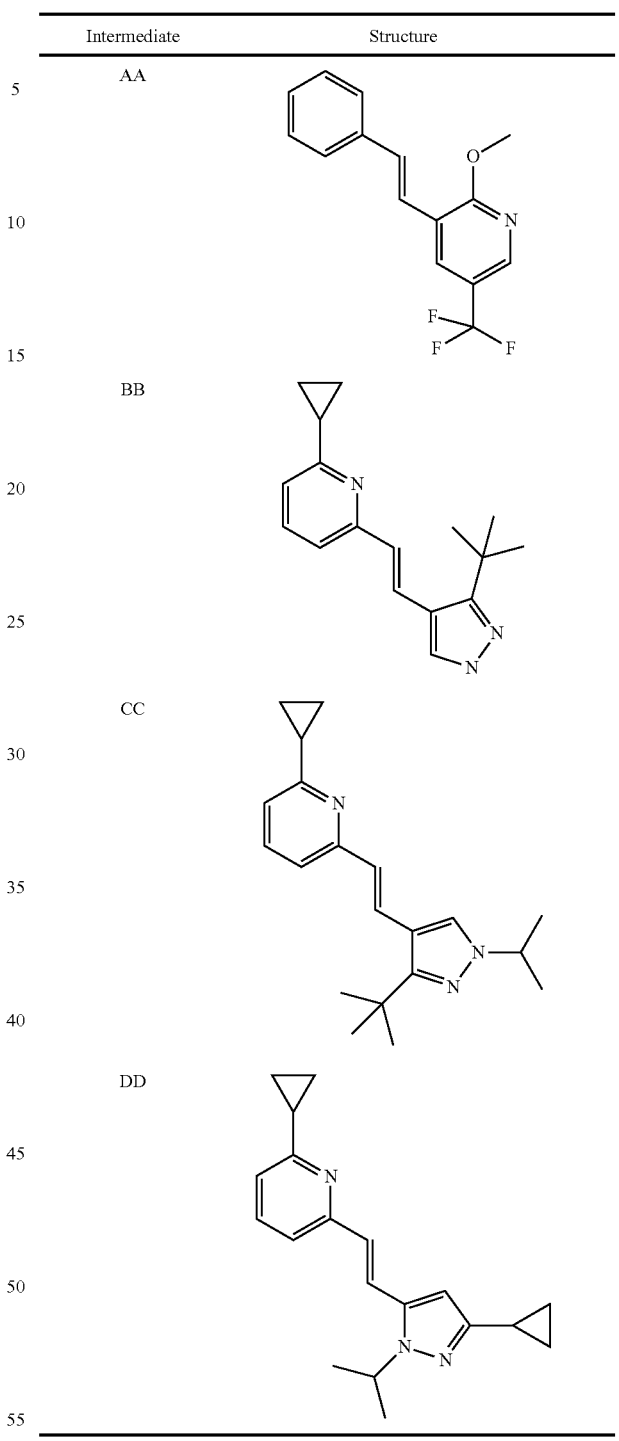
Method 4: Synthesis of Intermediate EE
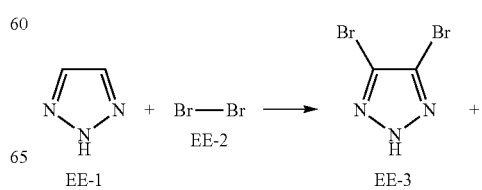

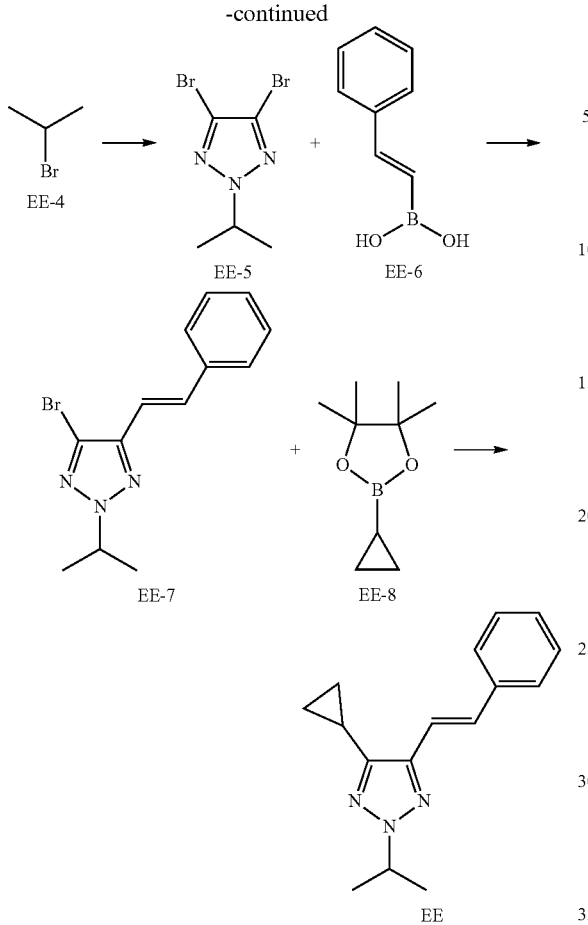

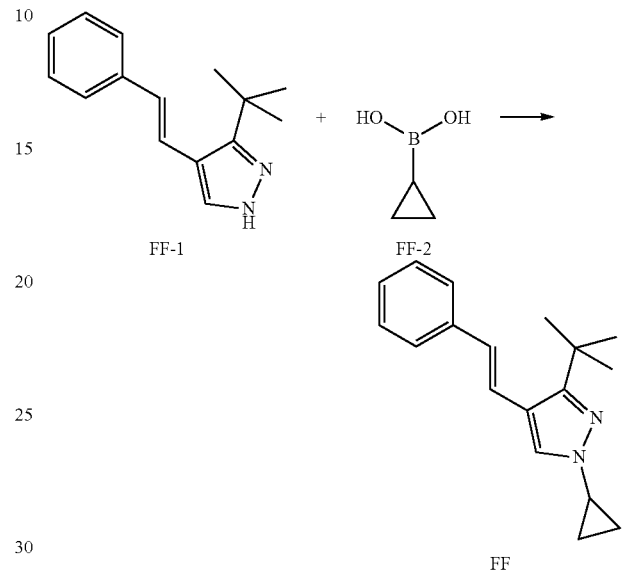

added and the reaction mixture is heated at 100° C. for 12 hours. The reaction mixture is quenched with water and extracted with EtOAc twice. The combined organics are concentrated. The residue is purified by column chromatography on silica gel eluting with EtOAc in heptane to yield Intermediate EE.

Method 5: Synthesis of Intermediate FF

To a stirred solution of EE-1 (10 g, 144.79 mmol) in water (100 mL) is added EE-2 (13.73 g, 173.75 mmol) dropwise at 0° C. and the reaction mixture is stirred at 0° C. for 7 hours. The reaction mixture is filtered and extracted with diethyl ether. The combined organics are concentrated in vacuo to yield EE-3.

To a stirred solution of EE-3 (10 g, 44.08 mmol) in DMF (60 mL) is added $K_2CO_3$ (9.158 g, 66.12 mmol) at room temperature then the reaction mixture is stirred at room temperature for 1 hour. EE-4 (5.422 g, 44.08 mmol) is added and the reaction mixture is stirred at room temperature for 12 hours. The reaction mixture is quenched with water then extracted with EtOAc twice. The organics are combined and concentrated. The residue is purified by column chromatography on silica gel eluting with EtOAc in heptane to yield Intermediate EE-5.

To a stirred solution of EE-5 (200 mg, 0.74 mmol) in Dioxane (5 mL) is added EE-6 (110 mg, 0.74 mmol) and $K_2CO_3$ (154 mg, 1.12 mmol). The mixture is degassed for 20 minutes then Pd2(dppf)Cl2 (61 mg, 0.074 mmol) is added and the reaction mixture is heated at 100° C. for 12 hours. The reaction mixture is quenched with water then extracted with EtOAc twice. The combined organics are concentrated and the residue is purified by column chromatography on silica gel eluting with EtOAc in heptane to yield Intermediate EE-7.

To a stirred solution of EE-7 (10 g, 34.23 mmol) in 1,4-dioxane (70 mL) is added EE-8 (6.23 g, 34.23 mmol) and $K_2CO_3$ (7.11 g, 51.34 mmol). The mixture is degassed for 20 minutes then $Pd_2(dppf)Cl_2$ (2.79 g, 3.42 mmol) is A solution of copper acetate (133 mg, 0.73 mmol) and 2,2'-dipyridyl (114 mg, 0.73 mmol) is warmed to 70° C. and then added dropwise to a suspension of FF-1 (138 mg, 0.61 mmol), FF-2 (131 mg, 1.52 mmol) and sodium carbonate (162 mg, 1.52 mmol) in DCE (6 mL) at room temperature. The reaction mixture is heated at 70° C. overnight. After this time, the reaction mixture is quenched with saturated NH4Cl aqueous solution then extracted with DCM twice. The organics are combined and washed with brine, dried over $Na_2SO_4$, filtered and concentrated.

The residue is purified by column chromatography on silica gel eluting with EtOAc in heptane to yield Intermediate FF.

The following intermediates are prepared in similar fashion:

| Intermediate | Structure |
|---|---|
| GG | 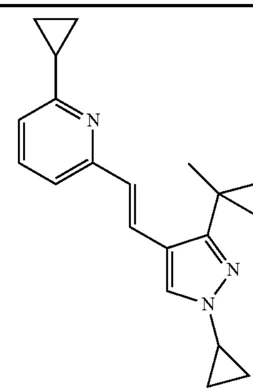 |

Method 6: Synthesis of Intermediate HH

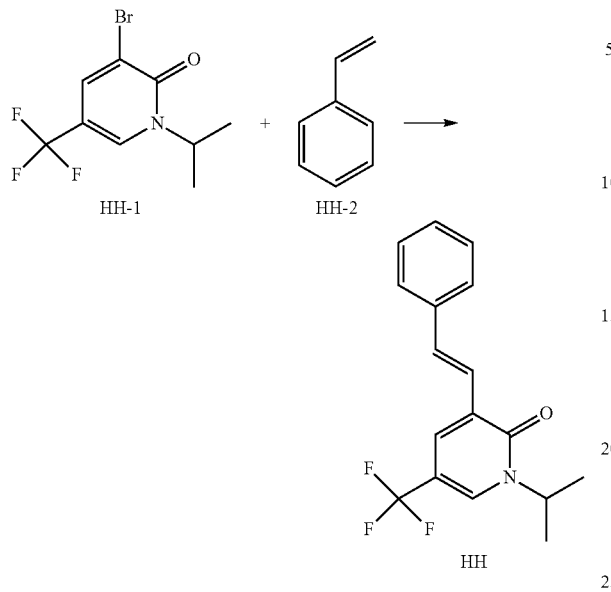

The mixture of HH-1 (500 mg, 1.76 mmol), HH-2 (0.81 mL, 7.04 mmol), N,N-dicyclohexylmethylamine (447 mg, 2.29 mmol), tri-tert-butylphosphonium tetrafluoroborate (26 mg, 0.09 mmol), Pd2(dba)3 (81 mg, 0.09 mmol) and lithium chloride (224 mg, 5.28 mmol) in dioxane (15 mL) is flushed with Ar, sealed then heated at 75° C. for 1.5 hours. The reaction mixture is filtered through diatomaceous earth then washed with EtOAc. The filtrate is concentrated then purified by column chromatography on silica gel eluting with EtOAc in heptane to yield Intermediate HH.

Method 7: Synthesis of Intermediate II

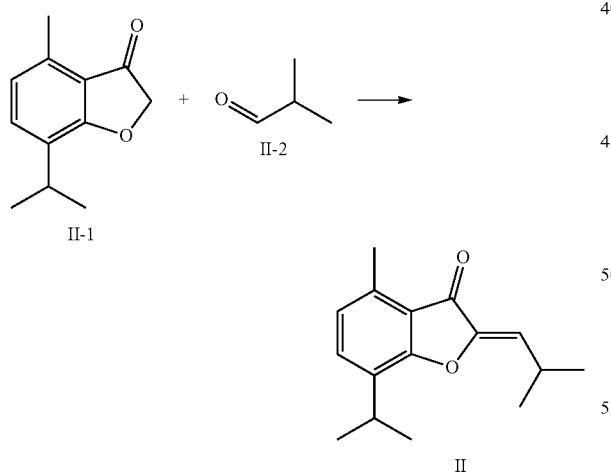

To a vigorously stirred solution of II-1 (320 mg, 1.68 mmol) in DCM (12 ml) is added 11-2 (0.19 ml, 2.1 mmol) and Al2O3 basic (5.1 g). The mixture is heated in a microwave reactor at 100° C. for 26 minutes. The reaction mixture is filtered and the solid residue is washed with DCM. The filtrate is concentrated to give alight yellow oil. The crude product is purified by column chromatography on silica gel eluting with EtOAc/Heptane to give Intermediate II.

Method 8: Synthesis of Intermediate JJ

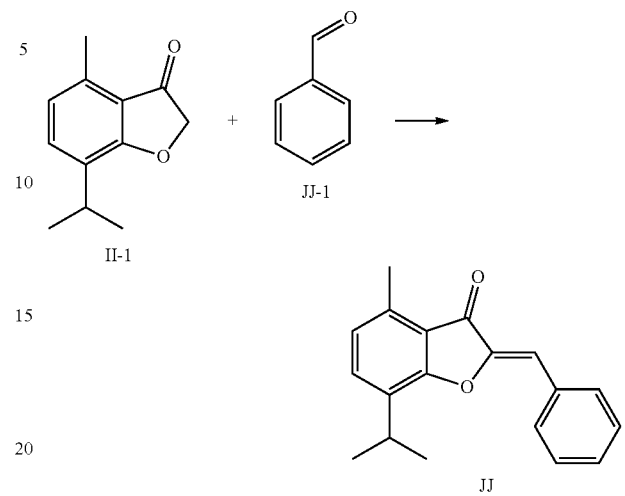

To a stirred solution of II-1 (600 mg, 3.15 mmol) in ethanol (10 ml) is added JJ-1 (335 mg, 3.15 mmol) and piperidine (0.031 ml, 0.315 mmol) at RT. The reaction mixture is stirred at 65° C. for 3 hours. The reaction mixture is then cooled down. The precipitates are collected by filtration and washed with EtOH and MTBE to give Intermediate JJ.

Method 9: Synthesis of Intermediate KK

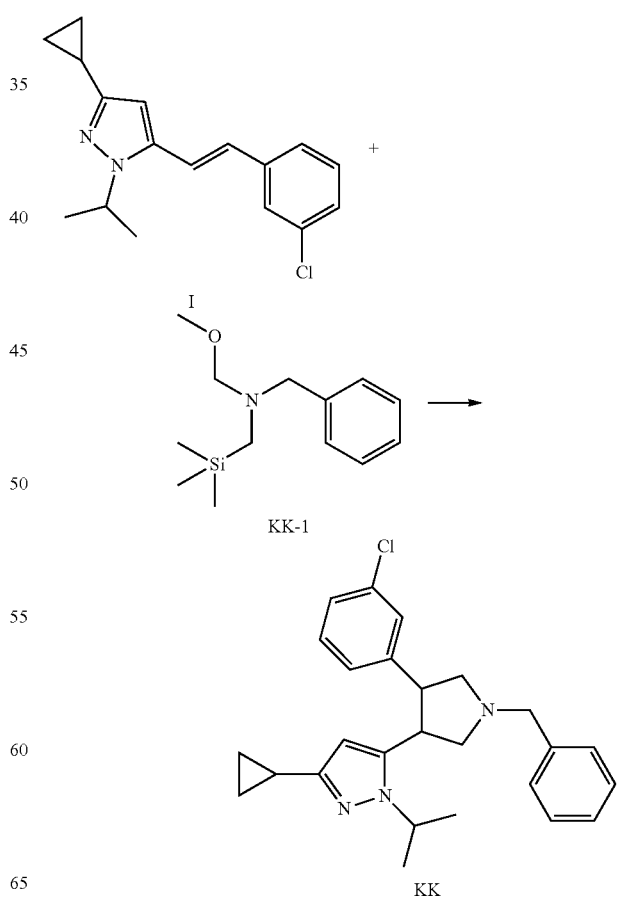

To a solution of I (752 mg, 2.62 mmol) in toluene (6 mL) is added TFA (0.015 mL) and KK-1 (1.61 mL, 6.29 mmol). The reaction mixture is stirred at room temperature for 2 hours. The reaction mixture is quenched with saturated NaHCO$_3$ aqueous solution then extracted with EtOAc twice. The organics are combined and washed with brine, dried over Na$_2$SO$_4$, filtered and concentrated. The residue is purified by column chromatography on silica gel eluting with EtOAc in heptane to yield Intermediate KK.

The following intermediates are prepared in similar fashion:

| Intermediate | Structure |
|---|---|
| LL | |
| MM | |
| NN | |
| OO | |
| PP | 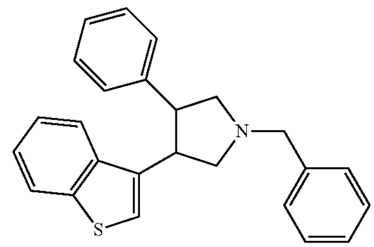 [SMILES: c1ccc(CN2CC(c3ccccc3)C(c3csc4ccccc34)C2)cc1] |
| QQ | 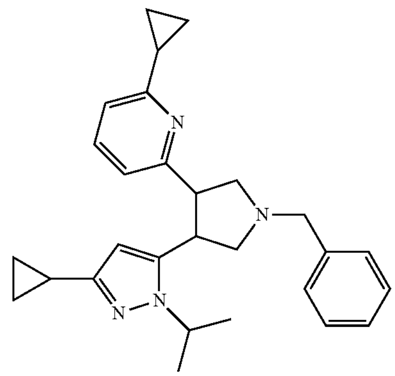 [SMILES: CC(C)n1nc(C2CC2)cc1C1CN(Cc2ccccc2)CC1c1cccc(C2CC2)n1] |
| RR | 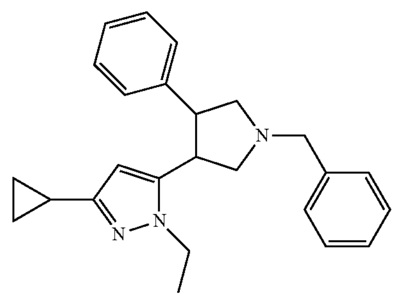 |
| SS | 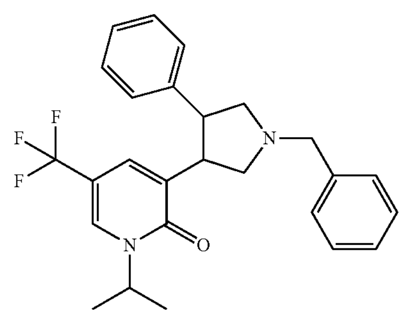 [SMILES: CC(C)n1cc(C(F)(F)F)cc(C2CN(Cc3ccccc3)CC2c2ccccc2)c1=O] |
| TT | 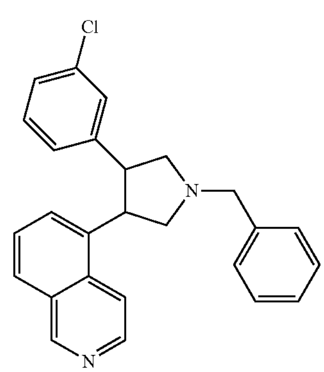 [SMILES: Clc1cccc(C2CN(Cc3ccccc3)CC2c2cccc3cnccc23)c1] |

| Intermediate | Structure |
|---|---|
| UU | 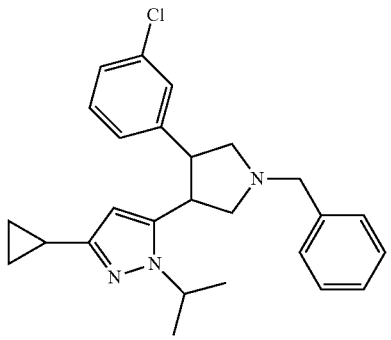 [SMILES: CC(C)n1nc(C2CC2)cc1C1CN(Cc2ccccc2)CC1c1cccc(Cl)c1] |
| VV | 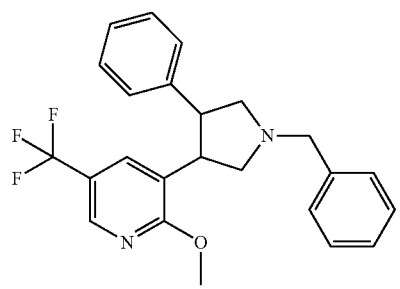 [SMILES: COc1ncc(C(F)(F)F)cc1C1CN(Cc2ccccc2)CC1c1ccccc1] |
| WW | 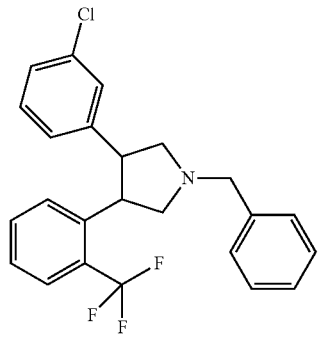 [SMILES: FC(F)(F)c1ccccc1C1CN(Cc2ccccc2)CC1c1cccc(Cl)c1] |
| XX | 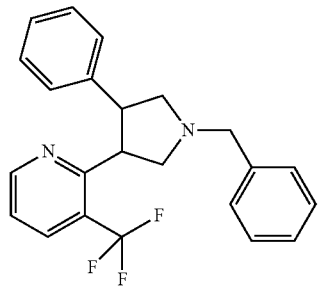 [SMILES: FC(F)(F)c1cccnc1C1CN(Cc2ccccc2)CC1c1ccccc1] |
| YY | 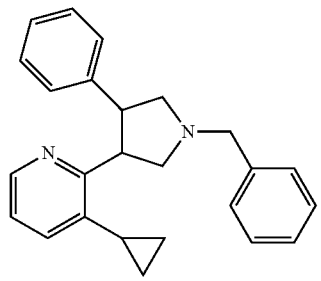 [SMILES: c1ccc(CN2CC(c3ccccc3)C(c3ncccc3C3CC3)C2)cc1] |

| Intermediate | Structure |
|---|---|
| ZZ | 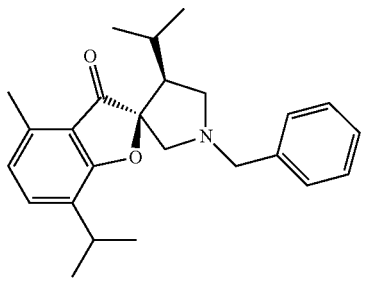 [SMILES: Cc1ccc(C(C)C)c2c1C(=O)[C@]1(CN(Cc3ccccc3)C[C@@H]1C(C)C)O2] |
| AAA | 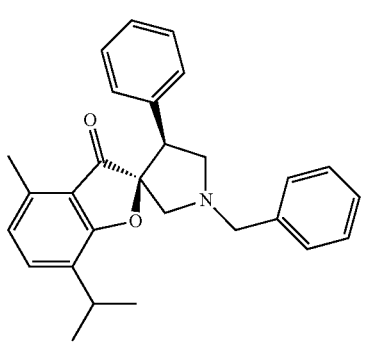 [SMILES: Cc1ccc(C(C)C)c2c1C(=O)[C@]1(CN(Cc3ccccc3)C[C@@H]1c1ccccc1)O2] |

Method 10: Synthesis of Intermediate BBB

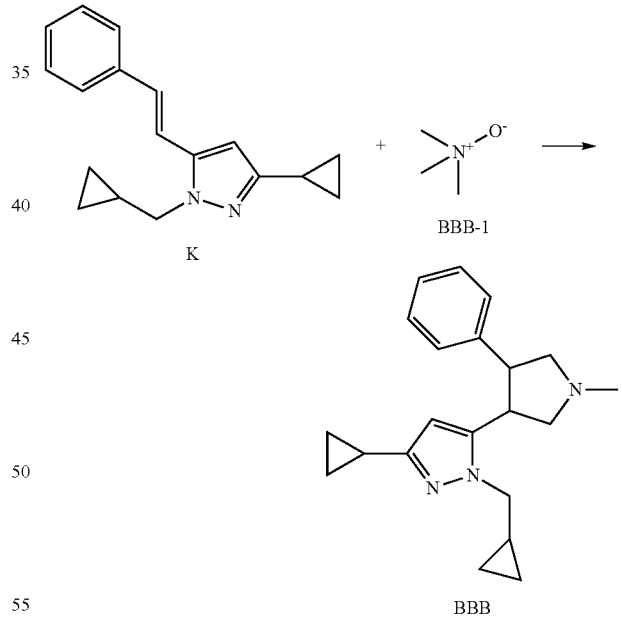

To a suspension of K (367 mg, 1.39 mmol) and BBB-1 (156.4 mg, 2.08 mmol) in THF (12 mL) at 0° C. is added LDA solution (2M in THF/ethyl benzene/heptane, 3.12 mL, 6.25 mmol). The reaction mixture is stirred at 0° C. for 30 minutes. The reaction mixture is quenched with water then extracted with EtOAc twice. The organics are combined and washed with brine, dried over $Na_2SO_4$, filtered and concentrated. The residue is purified by column chromatography on silica gel eluting with EtOAc in heptane to yield Intermediate BBB.

The following intermediates are prepared in similar fashion:
| Intermediate | Structure |
|---|---|
| CCC | 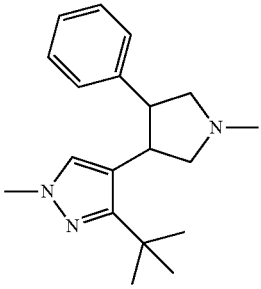 |
| DDD | 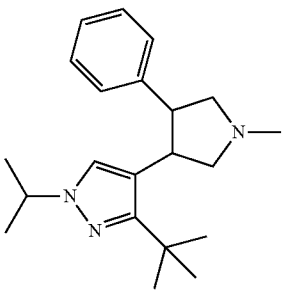 [SMILES: CC(C)n1cc(C2CN(C)CC2c2ccccc2)c(C(C)(C)C)n1] |
| EEE | 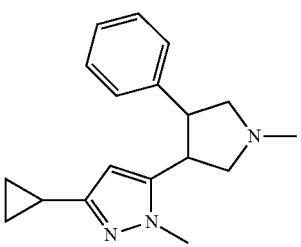 [SMILES: CN1CC(c2ccccc2)C(c2cc(C3CC3)nn2C)C1] |
| FFF | 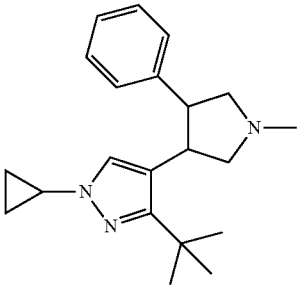 [SMILES: CN1CC(c2ccccc2)C(c2cn(C3CC3)nc2C(C)(C)C)C1] |
| GGG | 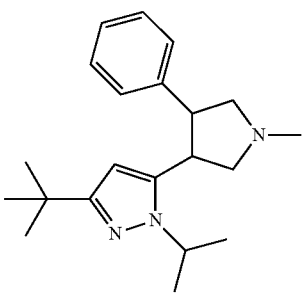 [SMILES: CC(C)n1nc(C(C)(C)C)cc1C1CN(C)CC1c1ccccc1] |
| HHH | 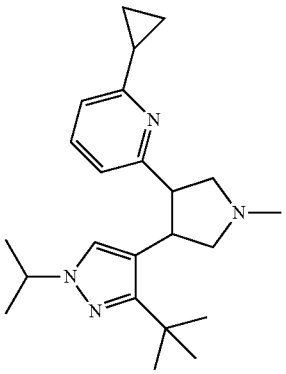 [SMILES: CC(C)n1cc(C2CN(C)CC2c2cccc(C3CC3)n2)c(C(C)(C)C)n1] |
| III | 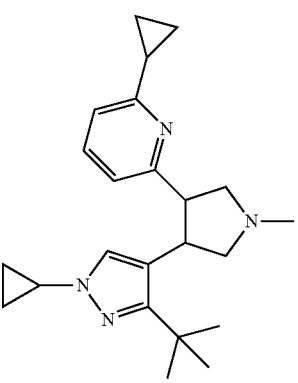 [SMILES: CN1CC(c2cccc(C3CC3)n2)C(c2cn(C3CC3)nc2C(C)(C)C)C1] |
| JJJ | 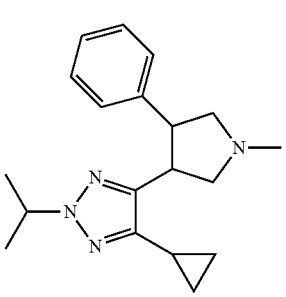 [SMILES: CC(C)n1nc(C2CC2)c(C2CN(C)CC2c2ccccc2)n1] |
| KKK | 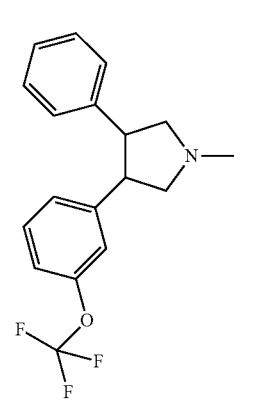 |

Method 11: Synthesis of Intermediate LLL

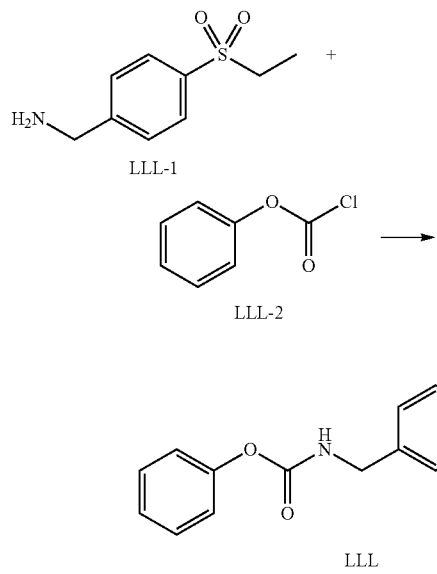

To a solution of LLL-1 (4 g, 16.97 mmol) in DMF (50 mL) at 0° C. is added pyridine (5.49 mL, 67.87 mmol) and followed by dropwise addition of LLL-2 (2.35 mL, 18.67 mmol). The reaction mixture is stirred at 0° C. for 1 hour. After this time, the reaction mixture is quenched with water and extracted with EtOAc twice. The organics are combined and washed with brine, dried over $Na_2SO_4$, filtered and concentrated. The residue is purified by column chromatography on silica gel eluting with EtOAc in heptane to yield Intermediate LLL. MS (ES+): m/z 320.5[ M+H]$^+$.

The following intermediates are synthesized in a similar fashion

| Intermediate | Structure |
|---|---|
| MMM | 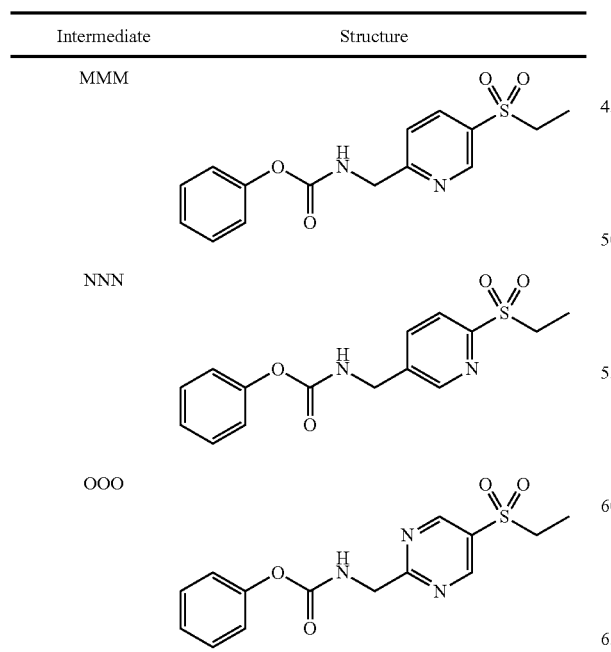 |
| NNN | 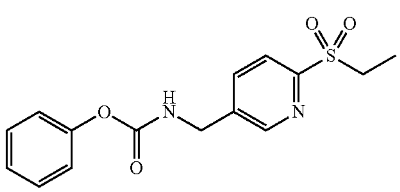 [SMILES: CCS(=O)(=O)c1ccc(CNC(=O)Oc2ccccc2)cn1] |
| OOO | 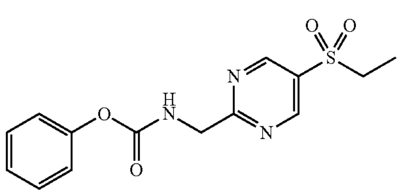 [SMILES: CCS(=O)(=O)c1cnc(CNC(=O)Oc2ccccc2)nc1] |
| PPP | 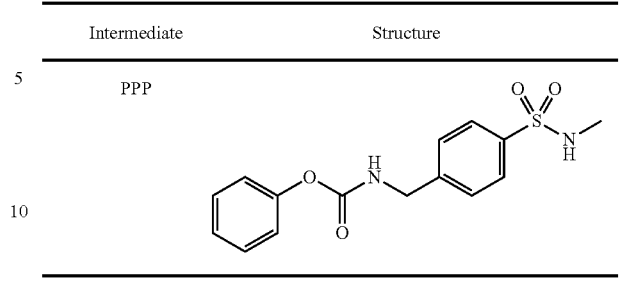 |

Method 12: Synthesis of Example 1

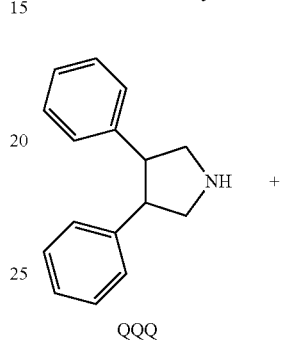

QQQ

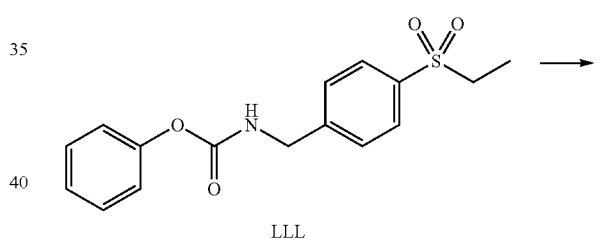

LLL

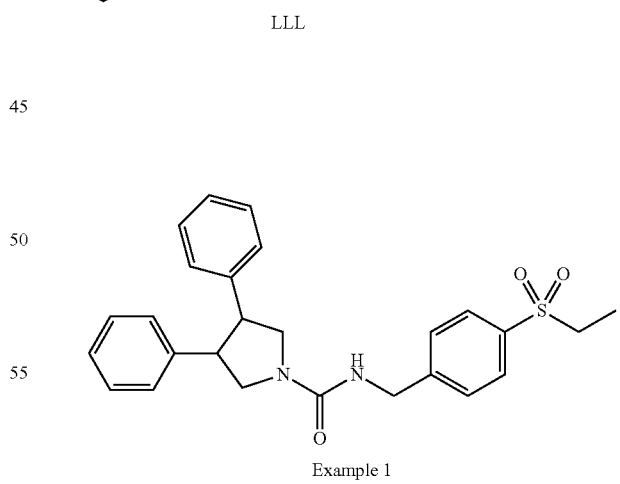

Example 1

To a solution of QQQ (50 mg, 0.22 mmol) in 1 ml DMSO is added TEA (0.06 ml, 0.45 mmol) followed by LLL (75 mg, 0.24 mmol). The mixture is heated at 60° C. for 2 hours. The reaction mixture is purified on preparative HPLC to give Example 1. MS (ES+): m/z 320.5 [M+H]$^+$.

Method 13: Synthesis of Example 48

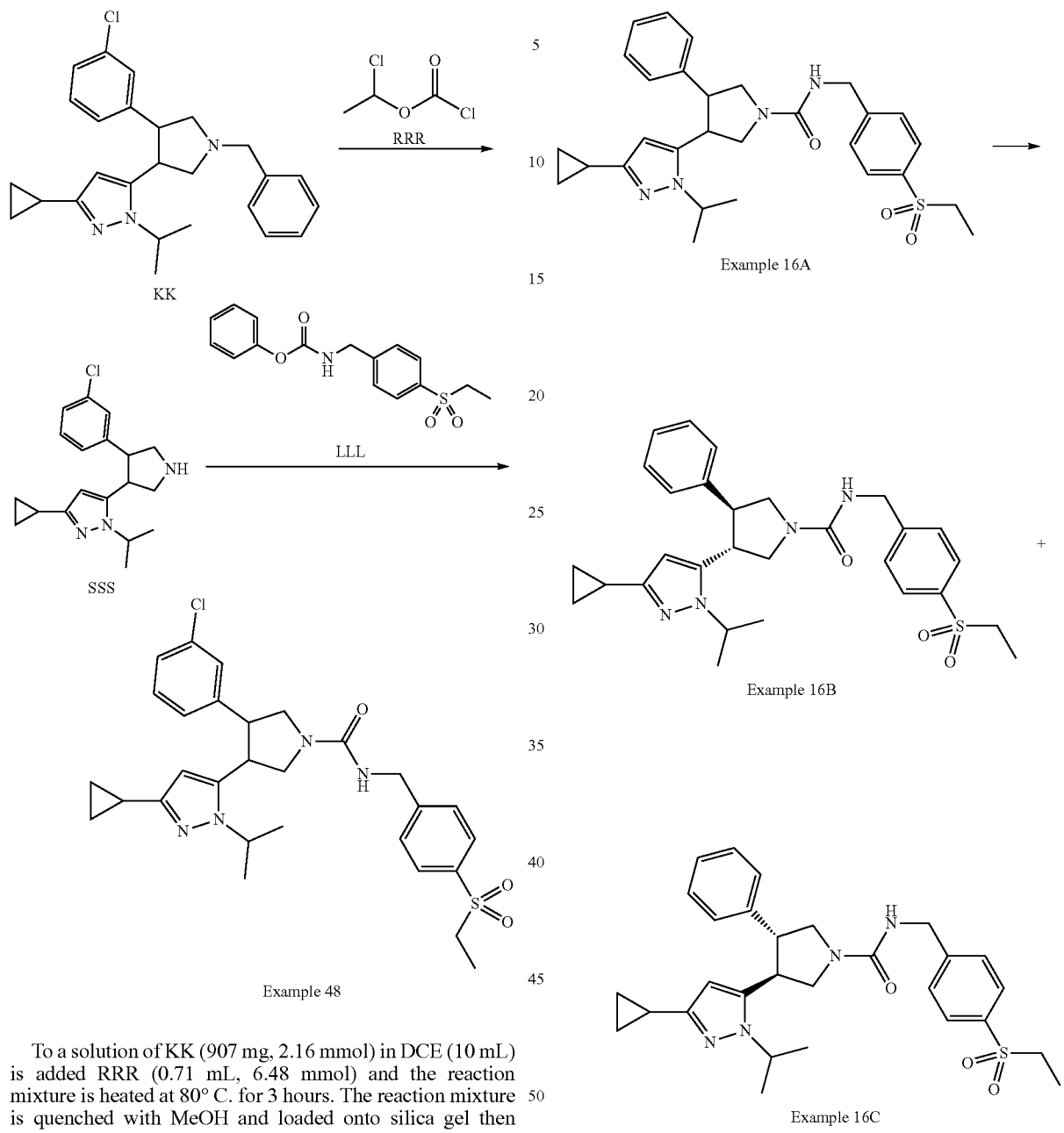

Example 48

To a solution of KK (907 mg, 2.16 mmol) in DCE (10 mL) is added RRR (0.71 mL, 6.48 mmol) and the reaction mixture is heated at 80° C. for 3 hours. The reaction mixture is quenched with MeOH and loaded onto silica gel then purified by column chromatography on silica gel eluting with MeOH in DCM (with NH3) to yield Intermediate SSS. MS (ES+): m/z 330.1 [M+H]$^+$. 102940-045, 102940-047.

To a solution of SSS (188 mg, 0.57 mmol) in DMSO (2.5 mL) is added TEA (0.24 mL, 1.71 mmol) and LLL (219 mg, 0.69 mmol). The reaction mixture is heated at 60° C. for 1 hour. After this time, the reaction mixture is quenched with water then extracted with EtOAc twice. The combined organics are washed with brine, dried over $Na_2SO_4$, filtered and concentrated. The residue is purified by column chromatography on silica gel eluting with MeOH in DCM to yield Example 48. MS (ES+): m/z 556.1 [M+H]$^+$.

The following Examples are synthesized in a similar fashion:

Example 4, 5, 7, 8, 10, 11, 12, 14, 15, 16, 17, 18, 20, 24, 32, 43, 45, 46, 48, 49, 53, 54 and 55.

Method: Chiral separation of Compound 16A

Example 16A

Example 16B

Example 16C

ChiralPak IC, 21×250 mm, 30%(1:1:1MeOH:EtOH:iPA): CO2, 90 ml/min, 120 bar, 35° C.

The absolute configuration of Compound 16C was determined as 1R,2S-enantiomer by vibrational circular dichroism (VCD) experiment.

All VCD measurements were performed on a ChiralIR spectrometer (BioTools, Fla., USA). The sample (Example 16C) was dissolved in $CDCl_3$ solution at the concentration of 30 mg/mL. Spectra were collected for 4 hours in a 200 μm path length cell. The final VCD spectra were corrected by subtracting the solvent spectra ($CDCl_3$) measured in the same conditions. The experimental VCD is in good agreement with 1R,2S-enatiomer.

Method 14: Synthesis of Example 28

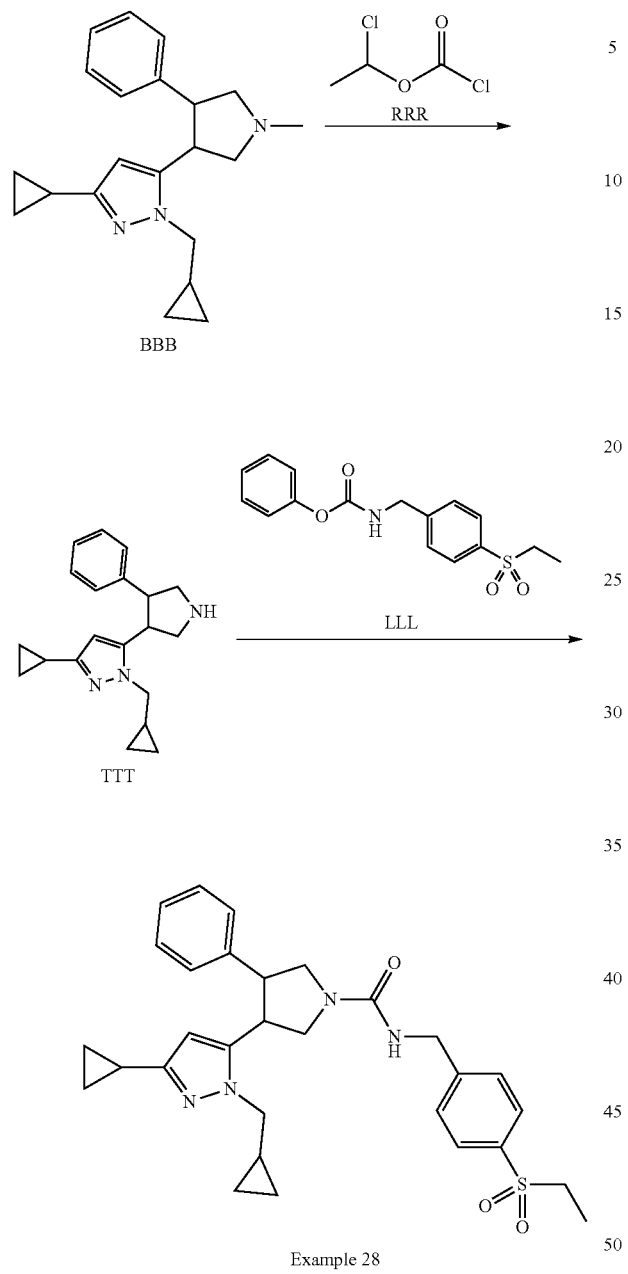

A solution of BBB (315 mg, 0.98 mmol) in neat RRR (3 mL) is heated in microwave reactor at 170° C. for 30 minutes. The reaction mixture is quenched with MeOH and loaded onto silica gel then purified by column chromatography on silica gel eluting with MeOH in DCM (with NH$_3$) to yield Intermediate TTT. MS (ES+): m/z 308.2 [M+H]$^+$. 102940-064

Example 28 is synthesized in a similar fashion as to Step 2 of Method 13. MS (ES+): m/z 533.4 [M+H]$^+$.

The following Examples are synthesized in a similar fashion:

Example 6, 9, 19, 23, 28, 29, 31, 32, 33, 34, 35, 38, 39, 41, 42, 56 and 57.

Method 15: Synthesis of Example 50

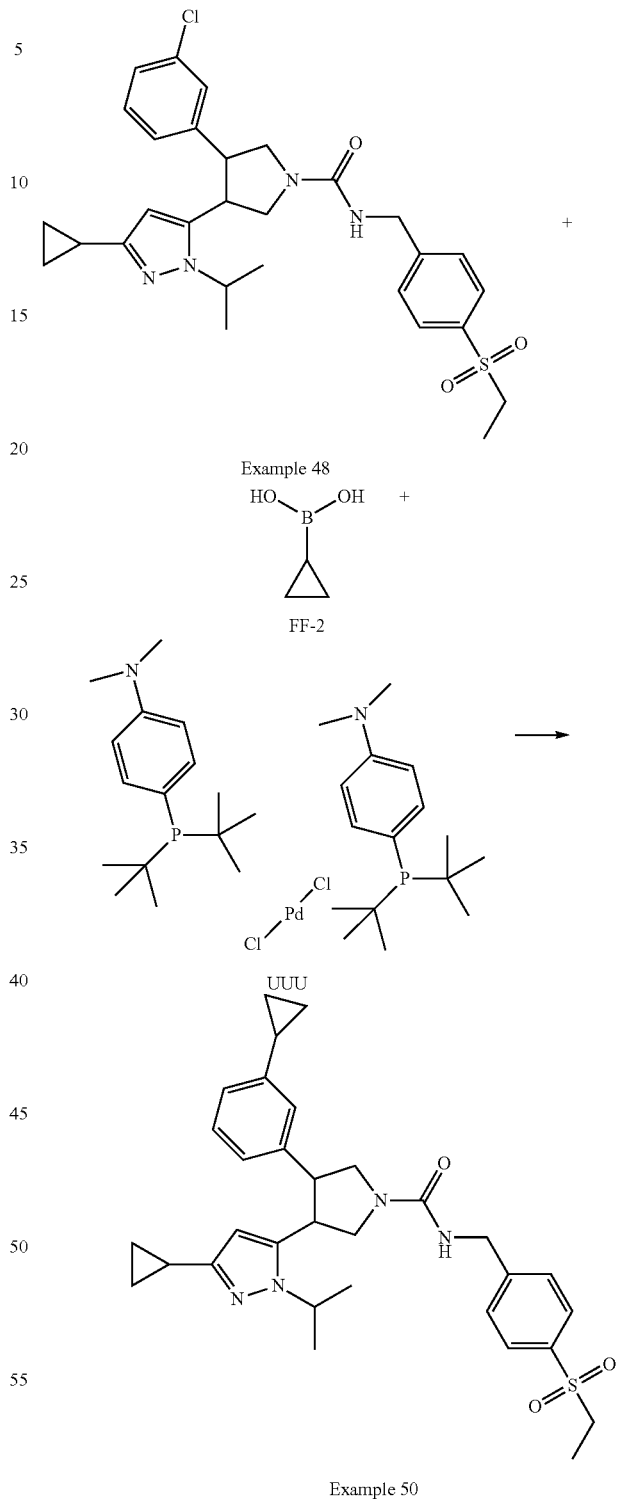

To a solution of Example 48 (100 mg, 0.18 mmol), FF-2 (46.4 mg, 0.54 mmol) and aqueous Na$_2$CO$_3$ solution (2M, 0.27 mL, 0.54 mmol) in Dioxane (1.5 mL) is added UUU (25.5 mg, 0.036 mmol). The reaction mixture is purged with Ar then sealed and heated at 130° C. for 1.5 hours. After this time, the reaction mixture is quenched with water then extracted with EA twice. The organics are combined and washed with brine, dried over Na$_2$SO$_4$, filtered and concentrated. The residue is purified by pre-HPLC to yield Example 50. MS (ES+): m/z 561.1 [M+H]$^+$.

The following compound, Example 54, was synthesized in a similar fashion

| Example | Structure | m/z [M + H]$^+$ | HPLC Method |
|---|---|---|---|
| 52 | 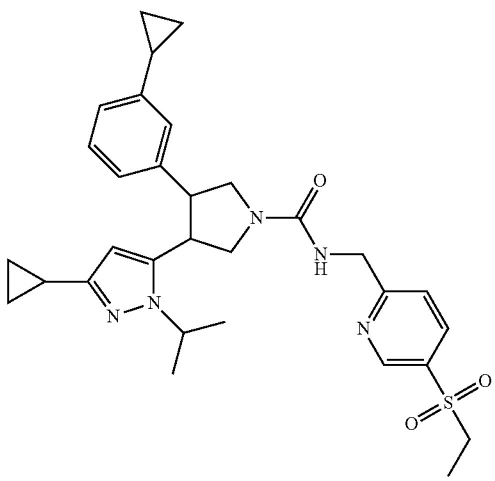 [SMILES: CCS(=O)(=O)c1ccc(CNC(=O)N2CC(c3cccc(C4CC4)c3)C(c3cc(C4CC4)nn3C(C)C)C2)nc1] | 562.4 | A |

Method 16: Synthesis of Intermediate VVV

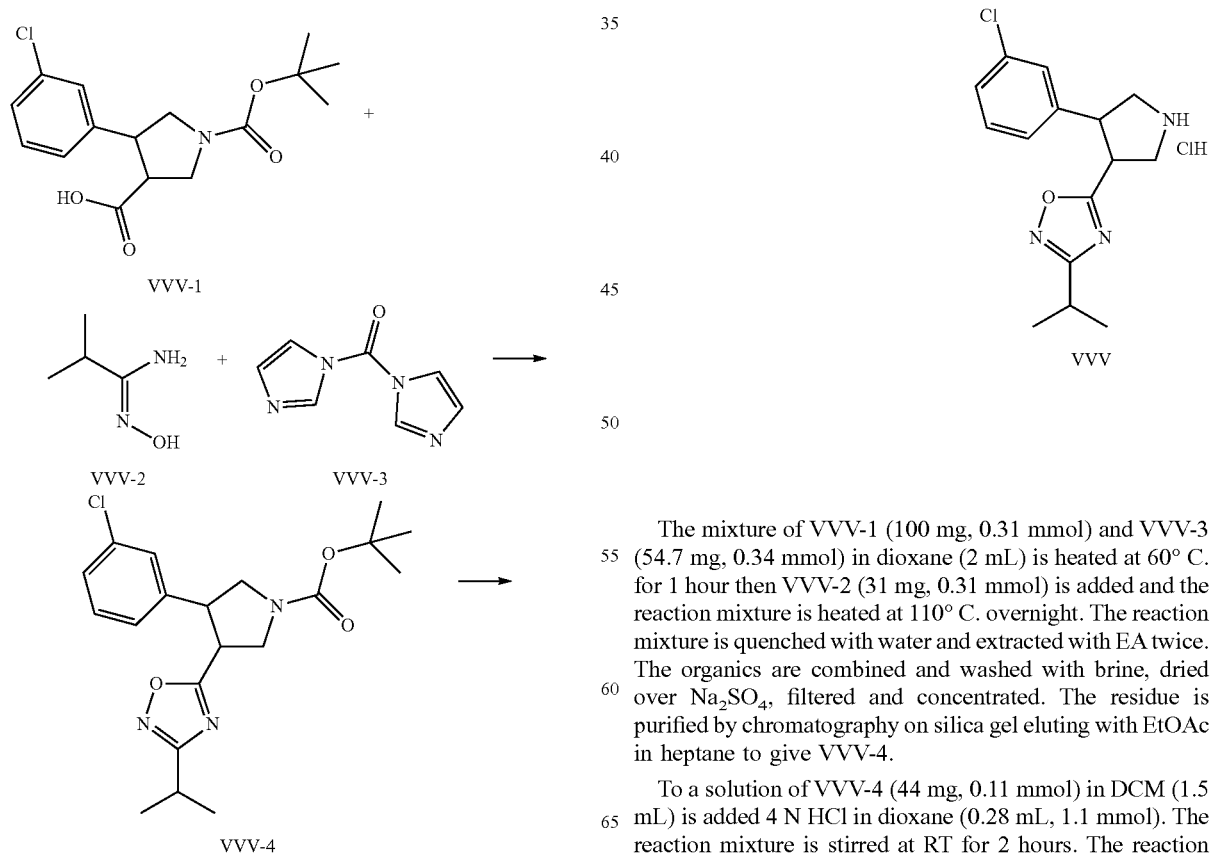

The mixture of VVV-1 (100 mg, 0.31 mmol) and VVV-3 (54.7 mg, 0.34 mmol) in dioxane (2 mL) is heated at 60° C. for 1 hour then VVV-2 (31 mg, 0.31 mmol) is added and the reaction mixture is heated at 110° C. overnight. The reaction mixture is quenched with water and extracted with EA twice. The organics are combined and washed with brine, dried over Na$_2$SO$_4$, filtered and concentrated. The residue is purified by chromatography on silica gel eluting with EtOAc in heptane to give VVV-4.

To a solution of VVV-4 (44 mg, 0.11 mmol) in DCM (1.5 mL) is added 4 N HCl in dioxane (0.28 mL, 1.1 mmol). The reaction mixture is stirred at RT for 2 hours. The reaction mixture is concentrated in vacuo to yield VVV.

Method 17: Synthesis of Intermediate WWW

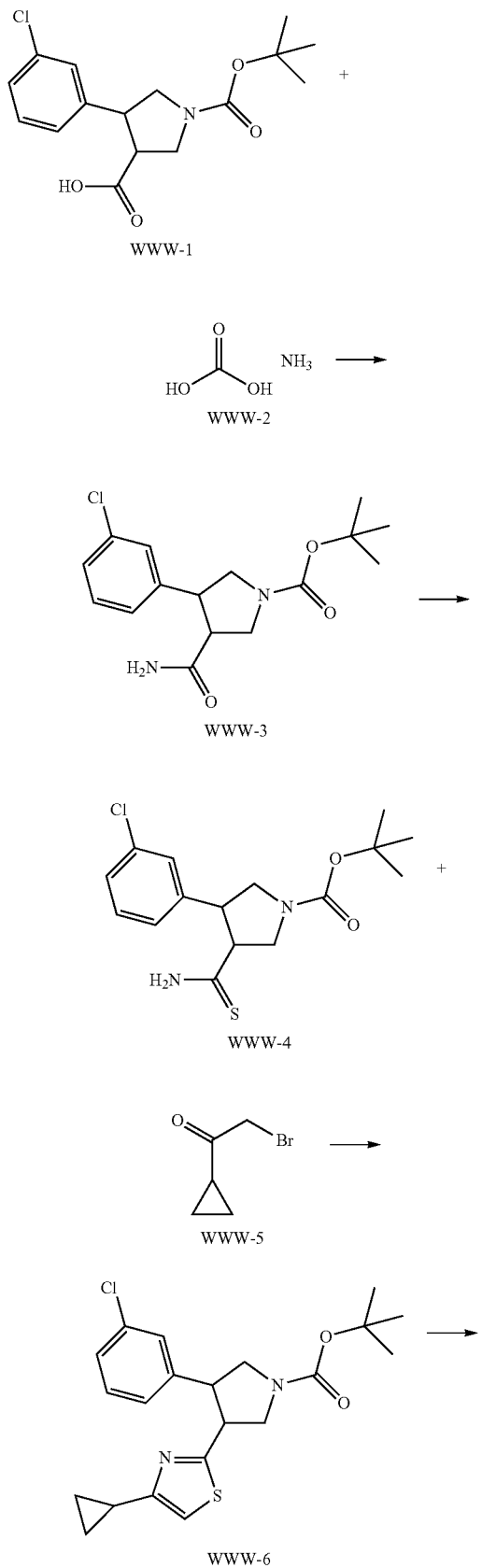

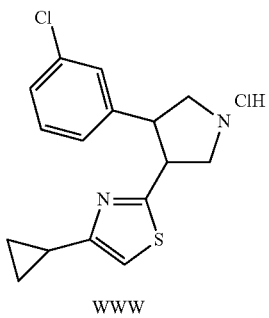

To a solution of WWW-1 (100 mg, 0.31 mmol) in DMF (1.5 mL) is added HATU (146 mg, 0.38 mmol), TEA (0.17 mL, 1.23 mmol) and WWW-2 (73 mg, 0.92 mmol). The reaction mixture is stirred at room temperature for 2 hours. The reaction mixture is quenched with water and extracted with EtOAc twice. The organics are combined and washed with brine, dried over $Na_2SO_4$, filtered and concentrated to yield WWW-3 which is used without purification.

To a solution of WWW-3 (100 mg, 0.31 mmol) in THF (3 mL) is added Lawesson's reagent (93 mg, 0.23 mmol) and the reaction mixture is heated at 80° C. for 4.5 hours. The reaction mixture is quenched with water and extracted with EtOAc twice. The organics are combined and washed with brine, dried over $Na_2SO_4$, filtered and concentrated. The residue is purified by chromatography on silica gel eluting with EtOAc in heptane to give WWW-4.

WWW-4 (42 mg, 0.12 mmol) and WWW-5 (20 mg, 0.12 mmol) are mixed in EtOH (1 mL) and the mixture is heated at 80° C. over the weekend. More CK-5 (40 mg, 0.24 mmol) is added followed by pyridine (0.03 mL) and the reaction mixture is heated at 80° C. overnight. The reaction mixture is concentrated and purified by chromatography on silica gel eluting with EtOAc in heptane to give WWW-6.

To a solution of WWW-6 (12 mg, 0.03 mmol) in DCM (1 mL) is added HCl (4N in dioxane, 0.074 mL, 0.3 mmol) and the reaction mixture is stirred at room temperature for 2 hours. The reaction mixture is concentrated to give Intermediate WWW.

Method 18: Synthesis of Example 13

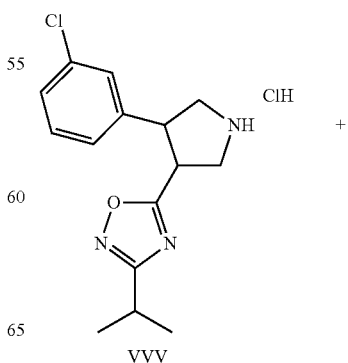

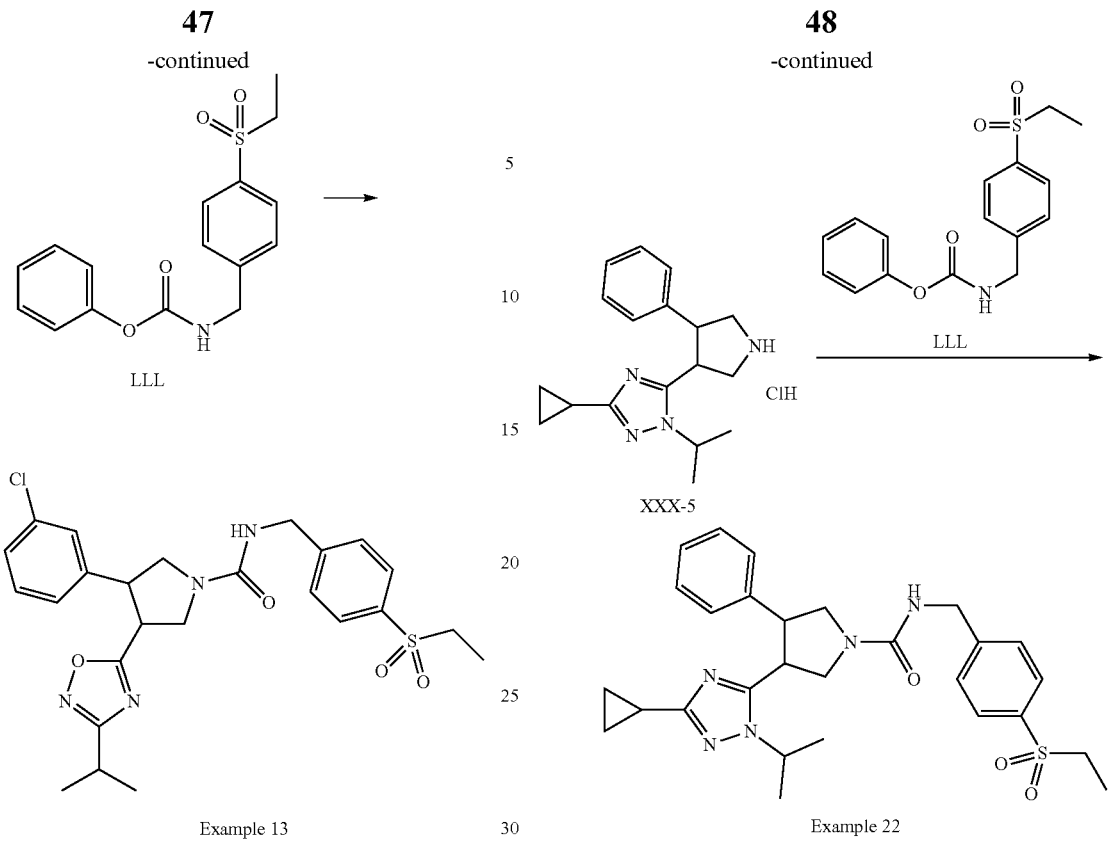

Example 13 is synthesized in a similar fashion as to Step 2 of Method 13. MS (ES+): m/z 515.2 [M−H]+.

Method 19: Synthesis of Example 22

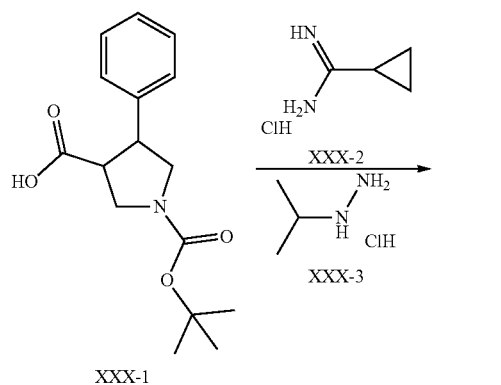

To a mixture of XXX-1 (200 mg, 0.686 mmol), XXX-2 (124.2 mg, 1.030 mmol), and HATU (287 mg, 0.755 mmol) is added DMF (8 mL) and DIEA (0.36 ml, 2.059 mmol). The reaction mixture is stirred at rt for 3 hours. To this solution is added XXX-3 (113.9 mg, 1.030 mmol) and AcOH (393.3 uL 10 eq.). The reaction mixture is heated to 80° C. and allowed to stir for an additional 3 hours. The solution is concentrated and purified to give XXX-4.

XXX-4 (150 mg, 0.378 mmol) is dissolved in DCM (8 mL) and to the resulting solution is added 4N HCl in Dioxane (0.5 mL). The solution is stirred at rt for 1 hour. The solution is concentrated and purified via HPLC to give XXX-5.

Example 22 is synthesized in a similar fashion as Step 2 of Method 13.

Method 20: Synthesis of Example 21, 36 and 42

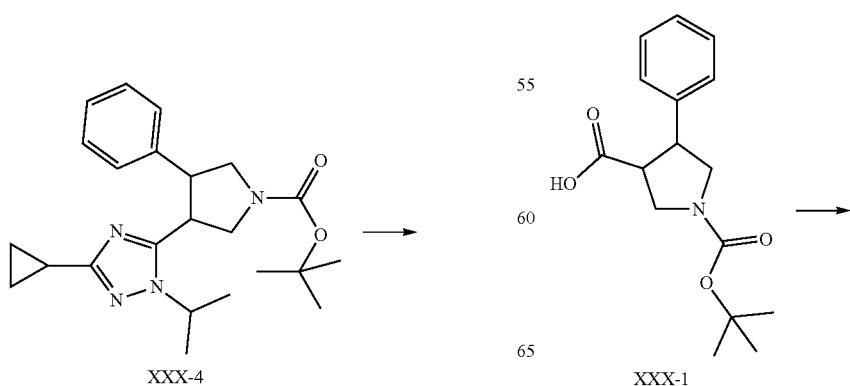

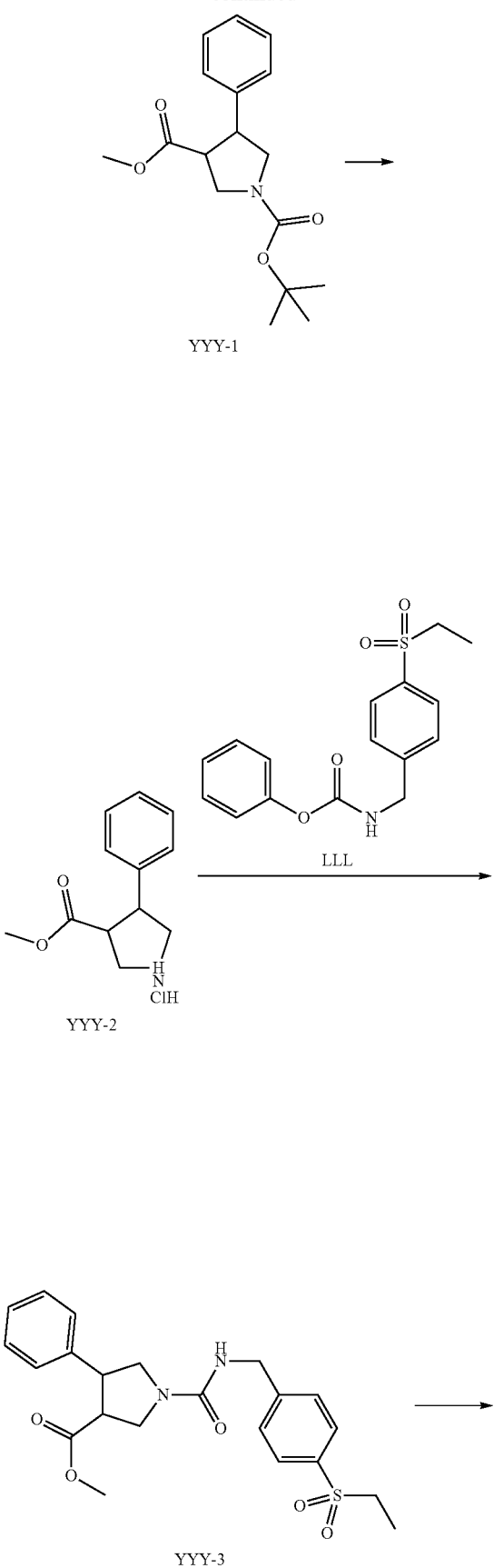

To a solution of XXX-1 (9.300 g, 31.9 mmol) in N,N-dimethylformamide (30 mL) is added NaH in mineral oil (60%, 2.553 g, 63.8 mmol) and the suspension is stirred at 0° C. for 10 min then MeI (6 mL, 95.8 mmol) is added and stirred for 1 hr. The reaction mixture is quenched with water and extracted with EtOAc. The organics are combined, washed with brine, and dried over MgSO$_4$, filtered and concentrated. The residue is purified by flash chromatography on silica gel eluting with EtOAc/Hex (0-30%) to give YYY-1.

To a solution of YYY-1 (9.5 g, 31.1 mmol) in DCM (100 ml) is added 4N HCl in dioxane (38.9 mL, 155.6 mmol) and the reaction mixture is stirred at RT overnight. The reaction mixture is concentrated in vacuo to obtain YYY-2.

To a YYY-2 (7.5 g, 31.0 mmol) in dimethylsulfoxide (50.000 ml) is added triethylamine (13 mL, 93.1 mmol) and LLL (9.9 g, 31.0 mmol). The reaction mixture is heated and stirred at 60° C. for 1 hour. The reaction is quenched with water and extracted with EtOAc twice. The organics are combined and washed with water then brine, dried over Na$_2$SO$_4$, filtered and concentrated. The residue is purified by chromatography using 100% EtOAc then MeOH/DCM (0-5%) to obtain YYY-3.

To a solution of YYY-3 (8.5 g, 19.7 mmol) in MeOH (60.000 ml) is added 3N NaOH aqueous solution (26.3 ml, 79 mmol) and the resulting solution is stirred at RT for 2 hours. Reaction mixture is concentrated in vacuo then diluted with water and 1N HCl aqueous solution is added to adjust pH to ~1 then the mixture is extracted with ethyl acetate. The organics are combined, dried over Mg₂SO₄, filtered and concentrated to obtain YYY-4.

YYY-4 (40 mg, 0.096 mmol) is dissolved in N,N-dimethylacetamide (1 ml). HATU (40.3 mg, 0.106 mmol) is added and the mixture is stirred to result a solution. To the resulting solution is added to cyclopropanecarboximidamide hydrochloride (17.4 mg, 144 mol), followed by diisopropylamine (51.830 µL, 0.288 mmol). The mixture is then shaken at rt for 3 hours.

A solution of t-butylhydrazine hydrochloride (18 mg, 144 µmol) in DMA (0.5 mL) is added followed by acetic acid (55 µL, 0.960 mmol). The mixture is shaken at 80° C. for 3 hours. The reaction mixture is purified by reverse phase HPLC to obtain Example 36.

YYY-4 (40 mg, 0.096 mmol) is dissolved in N,N-dimethylacetamide (1 ml). HATU (40.3 mg, 0.106 mmol) is added and the mixture is stirred to result in a solution. To the resulting solution is added 2-methylpropanimidamide hydrochloride (17.7 mg, 144 µmol), followed by diisopropylamine (51.830 µL, 0.288 mmol). The mixture is then shaken at rt for 3 hours.

A solution of t-butylhydrazine hydrochloride (18 mg, 144 µmol) in DMA (0.5 mL) is added followed by acetic acid (55 µL, 0.960 mmol). The mixture is shaken at 80° C. for 3 hours. The reaction mixture is purified by reverse phase HPLC to obtain Example 42.

YYY-4 (40 mg, 0.096 mmol) is dissolved in N,N-dimethylacetamide (1 ml). HATU (40.3 mg, 0.106 mmol) is added and the mixture is stirred to result a solution. To the resulting solution is added 2-methylpropanimidamide hydrochloride (17.7 mg, 144 µmol), followed by diisopropylamine (51.830 µL, 0.288 mmol). The mixture is then shaken at rt for 3 hours.

A solution of cyclopropylhydrazine (10.4 mg, 144 µmol) in DMA (0.5 mL) is added followed by acetic acid (55 µL, 0.960 mmol). The mixture is shaken at 80° C. for 3 hours. The reaction mixture is purified by reverse phase HPLC to obtain Example 21.

Method 21: Synthesis of Example 2

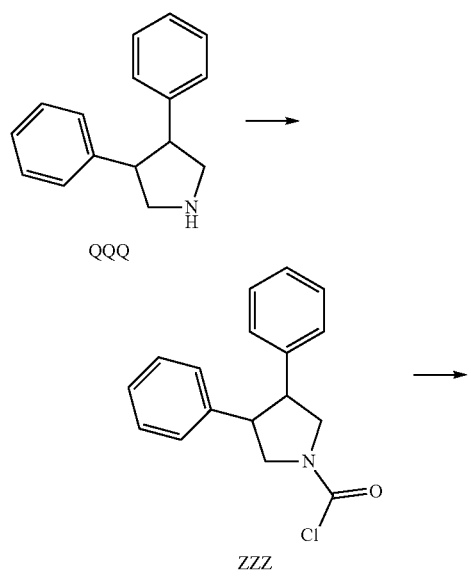

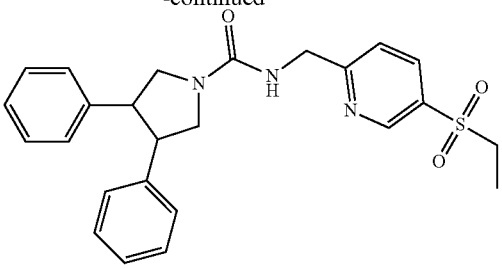

Example 2

To a solution of QQQ (1.3 g, 5.8 mmol) in dichloromethane (32.5 ml) was added NaHCO₃ (saturated solution) (32.500 ml) followed by phosgene (20% in toluene) (7.7 ml, 14.6 mmol). The mixture was stirred for 40 min before it was diluted with water. The layers separated and organic was concentrated to give trans-3,4-diphenylpyrrolidine-1-carbonyl chloride, which was used directly without further purification.

A solution of ZZZ (42 mg, 0.147 mmol) in N,N-dimethylacetamide (0.8 ml) is added to MMM (52.2 mg, 220 µmol) followed by diisopropylethylamine (106 µL, 0.588 mmol). The mixture is shaken at room temperature overnight, and then purified by reverse phase preparative HPLC to obtain Example 2.

Example 3 is prepared in the same way as described for Example 2.

Assessment of Biological Activity

The compounds of the present invention have activity as modulators of RORγ (retinoid acid receptor-related orphan receptor γ).

Reporter Gene Assay (RGA)

A nuclear receptor transactivation assay is performed to quantitate the ability of test compounds to inhibit RORγ transactivation of a luciferase reporter. A similar assay is described in: Khan et al., Bioorganic & Medicinal Chemistry Letters 23 (2013), 532-536. The system uses transiently transfected HEK 293 cells cotransfected with two plasmids (pGL4.3, luc2P/GAL4UAS/Hygro, and pBIND, Gal4DBD hRORC LBD1-3). The positive control is co-transiently transfected with both plasmids, and the negative control contains the pGL4.3 promoter sequence. Assays are assembled in 384 well plates where transiently transfected cells and test compound at varying concentrations are incubated for 20-24 h. The next day, assays plates are taken out and equilibrated at RT for 20-30 minutes. Bright-Glo™ Luciferase Assay System is used to detect Luciferase production. After addition of Bright GLO detection reagent, the plates are incubated at RT for 20 minutes. The plates are read on an Envision plate reader to measure luminescence signal. The RLU signal is converted to POC relative to control and blank wells.

Cell Seeding Media:
RPMI 1640-Invitrogen #11875135), 2.5% FBS-Invitrogen #26140, 1×Penicillin-Streptomycin-Gibco #15140
Compound dilution buffer:
1× HBSS-Invitrogen #14025126
Assay Plates: Greiner #781080-020
Bright Glo Luciferase Assay System: Promega #E2620
Thaw lysis buffer provided in kit, add 100 mL lysis buffer to substrate powder.

Table 2 presents the results obtained when the compounds of the present invention were tested in the above assay, demonstrating their activity as modulators of RORγ.

TABLE 2

| Example | RGA IC$_{50}$ (nM) |
|---|---|
| 1 | 2400 |
| 2 | 5000 |
| 3 | 7900 |
| 4 | 3900 |
| 5 | 2800 |
| 6 | 2600 |
| 7 | 1015 |
| 8 | 1750 |
| 9 | 1550 |
| 10 | 275 |
| 11 | 620 |
| 12 | 2100 |
| 13 | 19000 |
| 14 | 1000 |
| 15 | 565 |
| 16A | 625 |
| 16B | 925 |
| 16C | 1250 |
| 17 | 2300 |
| 18 | 2500 |
| 19 | 4100 |
| 20 | 5500 |
| 21 | 7400 |
| 22 | 8700 |
| 23 | 6200 |
| 24 | 13000 |
| 25 | 4900 |
| 26 | 850 |
| 27 | 2400 |
| 28 | 1060 |
| 29 | 830 |
| 30 | 5200 |
| 31 | 2200 |
| 32 | 1200 |
| 33 | 510 |
| 34 | 1300 |
| 35 | 1900 |
| 36 | 2600 |
| 37 | 440 |
| 38 | 780 |
| 39 | 965 |
| 40 | 1300 |
| 41 | 1450 |
| 42 | 1950 |
| 43 | 149 |
| 44 | 1150 |
| 45 | 260 |
| 46 | 3200 |
| 47 | 1400 |
| 48 | 775 |
| 49 | 1750 |
| 50 | 545 |
| 51 | 810 |
| 52 | 1485 |
| 53 | 1550 |
| 54 | 5200 |
| 55 | 1500 |
| 56 | 865 |
| 57 | 1050 |

Analytical Methods

RP-HPLC purification methods used anywhere from 0-100% acetonitrile in water containing 0.1% formic acid or 0.1% TFA and used one of the following columns:
 a) Waters Sunfire OBD C18 5 μM 30×150 mm column
 b) Waters XBridge OBD C18 5 μM 30×150 mm column
 c) Waters ODB C8 5 μM 19×150 mm column
 d) Waters Atlantis ODB C18 5 μM 19×50 mm column
 e) Waters Atlantis T3 OBD 5 μM 30×100 mm column
 f) Phenomenex Gemini Axia C18 5 μM 30×100 mm column UPLC/MS Methods:
Analytical UPLC/MS Analysis Method A:
Column: Waters CSH 2.1×50 mm C18 1.7 um column
Gradient:

| Time (min) | 0.05% Formic Acid in Water | 0.05% Formic Acid in ACN | Flow (mL/min) |
|---|---|---|---|
| 0 | 90 | 10 | 0.8 |
| 1.19 | 0 | 100 | 0.8 |
| 1.77 | 0 | 100 | 0.8 |

Analytical LC/MS Analysis Method B:
Column: Waters BEH 2.1×50 mm C18 1.7 um column
Gradient:

| Time (min) | 0.05% Formic Acid in Water | 0.05% Formic Acid in ACN | Flow (mL/min) |
|---|---|---|---|
| 0 | 90 | 10 | 0.8 |
| 4.45 | 0 | 100 | 0.8 |
| 4.58 | 0 | 100 | 0.8 |

Analytical LC/MS Analysis Method C:
Column: Waters BEH 2.1×50 mm C18 1.7 um column
Gradient:

| Time (min) | 95% Water, 5% ACN with 2.5 mM Ammonium Bicarbonate | 100% ACN | Flow (mL/min) |
|---|---|---|---|
| 0 | 90 | 10 | 0.8 |
| 1.19 | 5 | 95 | 0.8 |
| 1.77 | 5 | 95 | 0.8 |

Table 3 shows the retention times, m/z and LC/MS method used for compounds 1-57.

TABLE 3

| Example | Retention time | m/z | LC MS method |
|---|---|---|---|
| 1 | 0.93 | 449.6 | A |
| 2 | 0.92 | 450.3 | A |
| 3 | 0.92 | 450.3 | A |
| 4 | 0.70 | 466.9 | A |
| 5 | 0.89 | 490.0 | A |
| 6 | 0.84 | 493.5 | A |
| 7 | 1.07 | 505.2 | A |
| 8 | 0.93 | 507.3 | A |
| 9 | 1.01 | 509.4 | A |
| 10 | 2.98 | 513.3 | B |
| 11 | 2.81 | 514.2 | B |
| 12 | 1.87 | 515.2 | B |
| 13 | 1.01 | 515.2 M-1 | A |
| 14 | 0.97 | 518.1 | A |
| 15 | 0.94 | 521.3 | A |
| 16A | 2.06 | 521.3 | B |
| 16B | 0.88 | 521.4 | A |
| 16C | 0.85 | 521.7 | A |
| 17 | 0.87 | 522.4 | A |
| 18 | 0.88 | 522.3 | A |
| 19 | 1.09 | 522.3 | A |
| 20 | 0.86 | 522.7 | A |
| 21 | 0.86 | 522.5 | A |
| 22 | 0.85 | 522.5 | A |

TABLE 3-continued

| Example | Retention time | m/z | LC MS method |
|---|---|---|---|
| 23 | 1.03 | 523.3 | A |
| 24 | 1.85 | 523.1 | B |
| 25 | 1.03 | 530.5 | A |
| 26 | 1.20 | 533.2 | A |
| 27 | 1.05 | 533.2 | A |
| 28 | 1.18 | 533.4 | A |
| 29 | 1.14 | 533.6 | A |
| 30 | 1.01 | 534.2 | A |
| 31 | 1.13 | 534.4 | A |
| 32 | 0.74 | 534.2 | A |
| 33 | 1.13 | 535.1 | A |
| 34 | 1.00 | 536.3 | A |
| 35 | 0.98 | 536.3 | A |
| 36 | 0.94 | 536.6 | A |
| 37 | 1.00 | 536.9 | A |
| 38 | 1.25 | 537.0 | A |
| 39 | 1.04 | 538.3 | A |
| 40 | 0.95 | 538.3 | A |
| 41 | 1.20 | 538.3 | A |
| 42 | 0.99 | 538.6 | A |
| 43 | 1.10 | 547.1 | A |
| 44 | 1.01 | 548.2 | A |
| 45 | 1.05 | 548.1 | A |
| 46 | 1.24 | 550.2 | A |
| 47 | 0.99 | 551.6 | A |
| 48 | 1.05 | 556.1 | A |
| 49 | 0.96 | 557.2 | A |
| 50 | 2.58 | 561.1 | B |
| 51 | 0.93 | 564.4 | A |
| 52 | 1.25 | 562.4 | A |
| 53 | 1.02 | 563.3 | A |
| 54 | 1.90 | 564.3 | B |
| 55 | 1.10 | 576.3 | A |
| 56 | 0.98 | 576.4 | A |
| 57 | 1.06 | 578.3 | A |

Methods of Therapeutic Use

On the basis of their biological properties the compounds of formula (I) according to the invention, or their tautomers, racemates, enantiomers, diastereomers, mixtures thereof and the salts of all the above-mentioned forms are suitable for treating autoimmune and allergic disorders in that they exhibit good modulatory effect upon RORγ

The present invention is therefore directed to compounds of general formula (I), and the pharmaceutically acceptable salts thereof, and all tautomers, racemates, enantiomers, diastereomers, mixtures thereof, which are useful in the treatment of a disease and/or condition wherein the activity of RORγ modulators is of therapeutic benefit, including but not limited to the treatment of autoimmune or allergic disorders.

Such disorders that may be treated by the compounds of the invention include for example: rheumatoid arthritis, psoriasis, systemic lupus erythromatosis, lupus nephritis, systemic sclerosis, vasculitis, scleroderma, asthma, allergic rhinitis, allergic eczema, multiple sclerosis, juvenile rheumatoid arthritis, juvenile idiopathic arthritis, type I diabetes, Crohn's disease, ulcerative colitis, graft versus host disease, psoriatic arthritis, reactive arthritis, ankylosing spondylitis, atherosclerosis, uveitis and non-radiographic spondyloarthropathy.

Accordingly, a compound of formula I according to any of the embodiments described herein or a pharmaceutically acceptable salt thereof may be used for the preparation of a medicament for treating a disease or disorder mediated by aldosterone synthase, including diabetic nephropathy, glomerulosclerosis, glomerulonephritis, IGA nephropathy, nephritic syndrome focal segmental glomerulosclerosis (FSGS), hypertension, pulmonary arterial hypertension, Conn's syndrome, systolic heart failure, diastolic heart failure, left ventricular dysfunction, left ventricular stiffness and fibrosis, left ventricular filing abnormalities, arterial stiffness, atherosclerosis and cardiovascular morbidity associated with primary or secondary hyperaldosteronism, adrenal hyperplasia and primary and secondary hyperaldosteronism.

For therapeutic use, the compounds of the invention may be administered via a pharmaceutical composition in any conventional pharmaceutical dosage form in any conventional manner. Conventional dosage forms typically include a pharmaceutically acceptable carrier suitable to the particular dosage form selected. Routes of administration include, but are not limited to, intravenously, intramuscularly, subcutaneously, intrasynovially, by infusion, sublingually, transdermally, orally, topically or by inhalation. The preferred modes of administration are oral and intravenous.

The compounds of this invention may be administered alone or in combination with adjuvants that enhance stability of the inhibitors, facilitate administration of pharmaceutical compositions containing them in certain embodiments, provide increased dissolution or dispersion, increase inhibitory activity, provide adjunct therapy, and the like, including other active ingredients. In one embodiment, for example, multiple compounds of the present invention can be administered. Advantageously, such combination therapies utilize lower dosages of the conventional therapeutics, thus avoiding possible toxicity and adverse side effects incurred when those agents are used as monotherapies. Compounds of the invention may be physically combined with the conventional therapeutics or other adjuvants into a single pharmaceutical composition. Advantageously, the compounds may then be administered together in a single dosage form. In some embodiments, the pharmaceutical compositions comprising such combinations of compounds contain at least about 5%, but more preferably at least about 20%, of a compound of formula (I) (w/w) or a combination thereof. The optimum percentage (w/w) of a compound of the invention may vary and is within the purview of those skilled in the art. Alternatively, the compounds of the present invention and the conventional therapeutics or other adjuvants may be administered separately (either serially or in parallel). Separate dosing allows for greater flexibility in the dosing regime.

As mentioned above, dosage forms of the compounds of this invention may include pharmaceutically acceptable carriers and adjuvants known to those of ordinary skill in the art and suitable to the dosage form. These carriers and adjuvants include, for example, ion exchangers, alumina, aluminum stearate, lecithin, serum proteins, buffer substances, water, salts or electrolytes and cellulose-based substances. Preferred dosage forms include tablet, capsule, caplet, liquid, solution, suspension, emulsion, lozenges, syrup, reconstitutable powder, granule, suppository and transdermal patch. Methods for preparing such dosage forms are known (see, for example, H. C. Ansel and N. G. Popovish, *Pharmaceutical Dosage Forms and Drug Delivery Systems*, 5th ed., Lea and Febiger (1990)). Dosage levels and requirements for the compounds of the present invention may be selected by those of ordinary skill in the art from available methods and techniques suitable for a particular patient. In some embodiments, dosage levels range from about 1-1000 mg/dose for a 70 kg patient. Although one dose per day may be sufficient, up to 5 doses per day may be given. For oral doses, up to 2000 mg/day may be required. As the skilled artisan will appreciate, lower or higher doses may be required depending on particular factors. For instance, specific dosage and treatment regimens will depend on factors such as the patient's general health profile, the severity and course of the patient's disorder or disposition thereto, and the judgment of the treating physician.

What is claimed is:

1. A compound of formula I

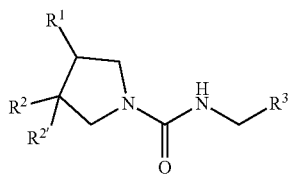

I wherein:
$R^{2'}$ is H; and
$R^1$ and $R^2$ are independently selected from benzothiophen-3-yl, isoquinolinyl, [1,2,4]-oxadiazolyl, phenyl, pyrazolyl, pyridyl, thiazolyl, 1H-[1,2,4]triazolyl and 2H-[1,2,3]triazolyl, wherein when $R^1$ is phenyl, then $R^2$ is other than phenyl;
or
$R^2$ and $R^{2'}$ form a spiro benzofuran-3-one ring; and
$R^1$ is selected from $C_{1-6}$alkyl, benzothiophen-3-yl, isoquinolinyl, [],2,41-oxadiazolyl, phenyl, pyrazolyl, pyridyl, thiazolyl, 1H-[1,2,4]triazolyl and 2H-[1,2,3]triazolyl;
wherein $R^1$ and $R^2$ are each optionally substituted by one to two groups independently selected from $C_{1-4}$alkyl, $C_{3-5}$ cycloalkyl, cyclopropylmethyl, —$CF_3$, halogen, —$OCF_3$, —OH, -$OCH_3$ and phenyl;
$R^3$ is selected from phenyl, pyridyl and pyrimidinyl;
wherein $R^3$ is substituted with a group selected from —$SO_2C_{1-3}$ alkyl and —$SO_2$ $NHC_{1-3}$alkyl;
or an enantiomer or a salt thereof.

2. The compound of formula (I) according to claim 1, wherein $R^{2'}$ is H; and
$R^1$ and $R^2$ are independently selected from benzothiophen-3-yl, isoquinolin-5-yl, [1,2,4]-oxadiazol-5-yl, phenyl, 4- and 5-pyrazolyl, 2- and 3-pyridyl, thiazol-2-yl, 1H-[1,2,4]triazol-5-yl and 2H-[1,2,3]triazol-5-yl, wherein when $R^1$ is phenyl, then $R^2$ is other than phenyl;
or
$R^2$ and $R^{2'}$ may form a spiro benzofuran-3-one ring; and
$R^1$ is selected from isopropyl, benzothiophen-3-yl, isoquinolin-5-yl, [1,2,41]-oxadiazol-5-yl, phenyl, 4- and 5-pyrazolyl, 2- and 3-pyridyl, thiazol-2-yl, 1H-[1,2,4] triazol-5-yl and 2H-[1,2,3]triazol-5-yl;
$R^1$ and $R^2$ are each optionally substituted by one to two groups independently selected from $C_{1-4}$alkyl, $C_{3-5}$ cycloalkyl, cyclopropylmethyl, —$CF_3$, Cl, —$OCF_3$, —OH, -$OCH_3$ and phenyl;
$R^3$ is selected from phenyl, 2- and 3-pyridyl and 2-pyrimidinyl;
wherein $R^3$ is substituted with a group selected from —$SO_2CH_2CH_3$ and —$SO_2NHCH_3$;
or an enantiomer or a salt thereof.

3. The compound of formula (I) according to claim 1, wherein $R^{2'}$ is H; and
$R^1$ and $R^2$ are independently selected from benzothiophen-3-yl, isoquinolin-5-yl, phenyl, 4- and 5-pyrazolyl, 2-pyridyl and 1H-[1,2,4]triazol-5-yl, wherein when $R^1$ is phenyl, then $R^2$ other than phenyl;
or
$R^2$ and $R^{2'}$ may form a spiro benzofuran-3-one ring; and
$R^1$ is selected from isopropyl, benzothiophen-3-yl, isoquinolin-5-yl, phenyl, 4- and 5-pyrazolyl, 2-pyridyl and 1H-[1,2,4]triazol-5-yl;
wherein $R^1$ and $R^2$ are each optionally substituted by one to two groups independently selected from $C_{1-4}$alkyl, $C_{3-5}$cycloalkyl, cyclopropylmethyl, —$CF_3$, Cl, —$OCF_3$, —OH and -$OCH_3$;
$R^3$ is selected from phenyl and 2-pyridyl;
wherein $R^3$ is substituted with a group selected from —$SO_2CH_2CH_3$ and —$SO_2NHCH_3$;
or an enantiomer or a salt thereof.

4. The compound of formula (I) according to claim 1, wherein $R^{2'}$ is H; and
$R^1$ and $R^2$ are independently selected from isopropyl, phenyl, 4- and 5-pyrazolyl and 2-pyridyl, wherein when $R^1$ is phenyl, then $R^2$ is other than phenyl;
or
$R^2$ and $R^{2'}$ may form a spiro benzofuran-3-one ring; and
$R^1$ is selected from isopropyl and phenyl;
wherein $R^1$ and $R^2$ are each optionally substituted by one to two groups independently selected from methyl, isopropyl, tert-butyl, cyclopropyl, cyclopentyl, —$CF_3$, Cl and —OCF3;
$R^3$ is selected from phenyl and 2-pyridyl;
wherein $R^3$ is substituted with a group selected from —$SO_2CH_2CH_3$ and —$SO_2NHCH_3$;
or an enantiomer or a salt thereof.

5. The compound according to claim 1 selected from the group consisting of

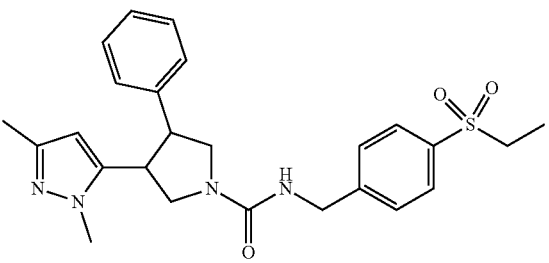

4

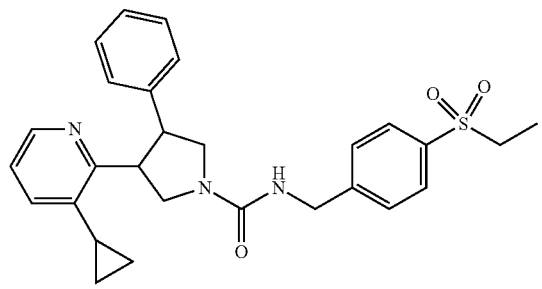

5

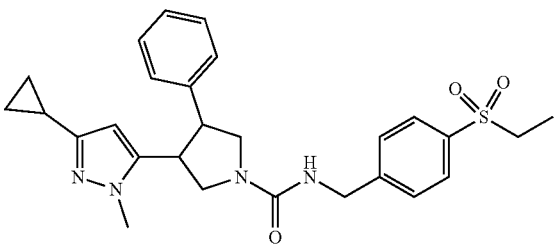

6

7
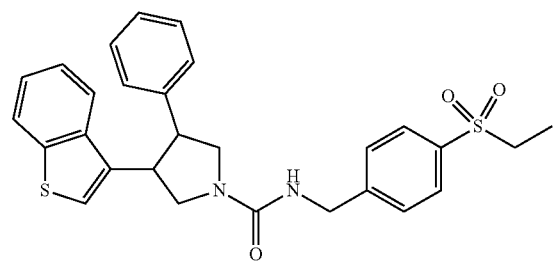
8
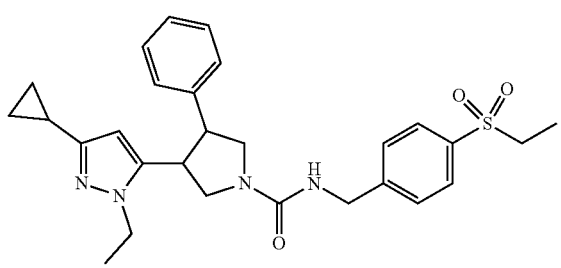
9
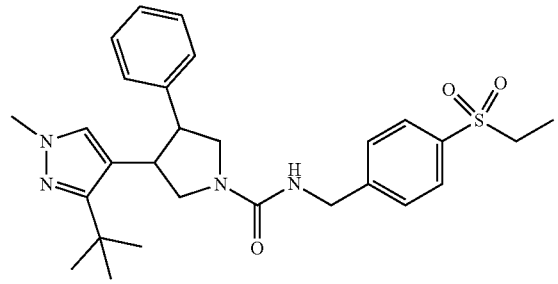
10
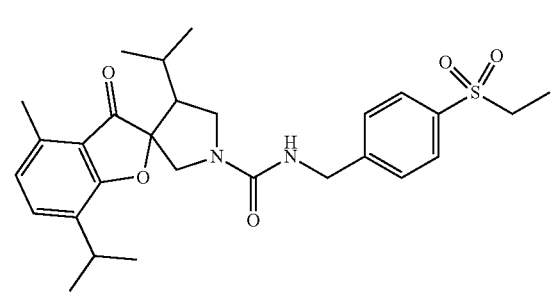
11
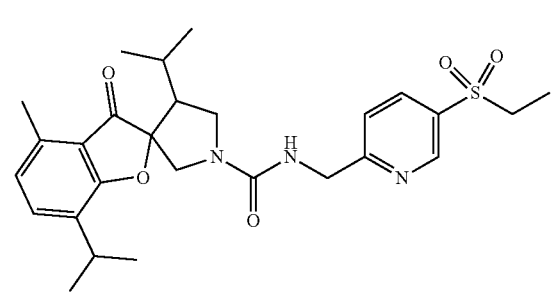
12
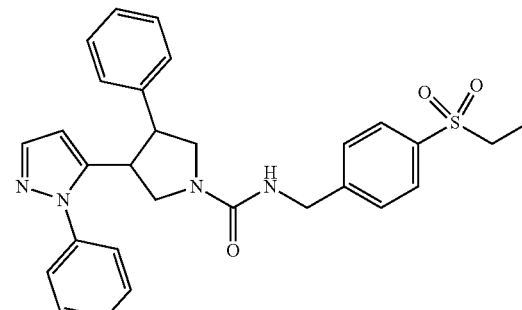
13
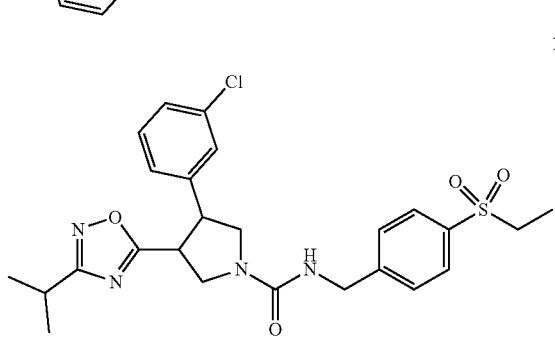
14
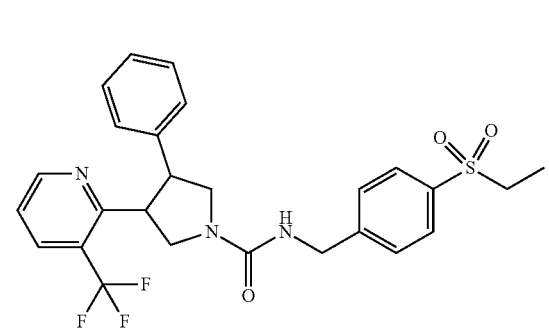
15
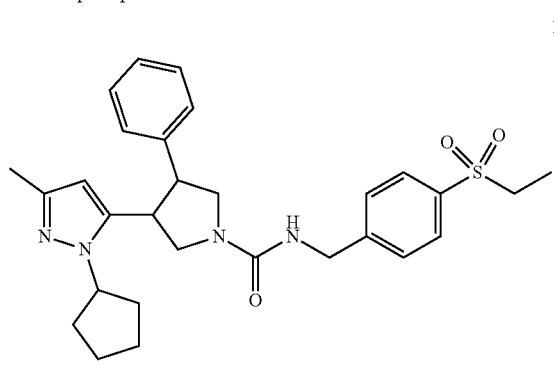
16A
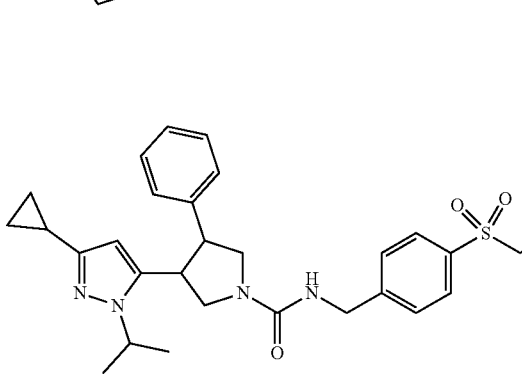

16B
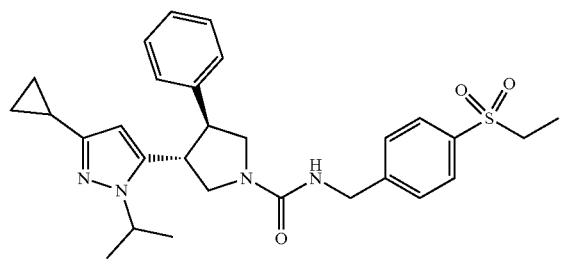
16C
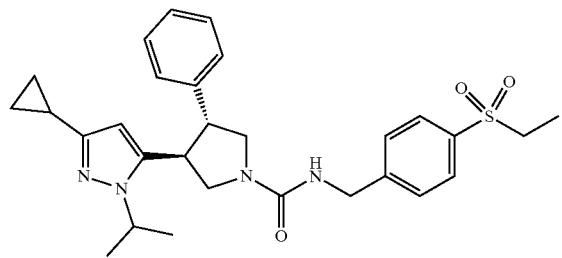
17
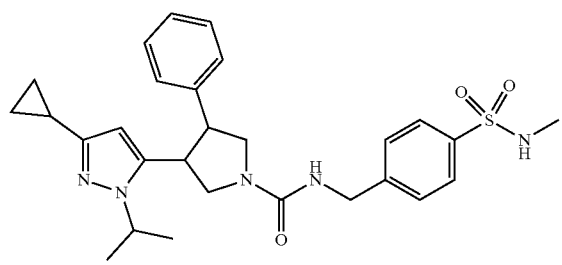
18
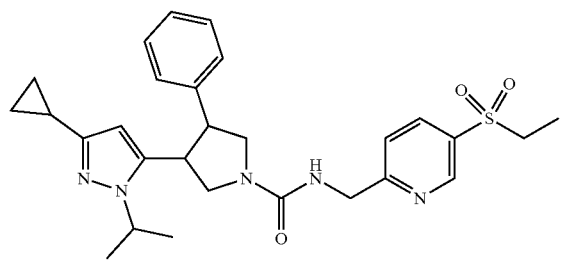
19
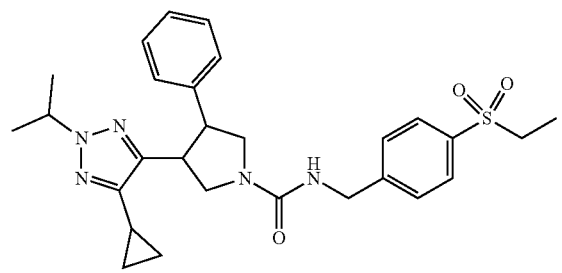
20
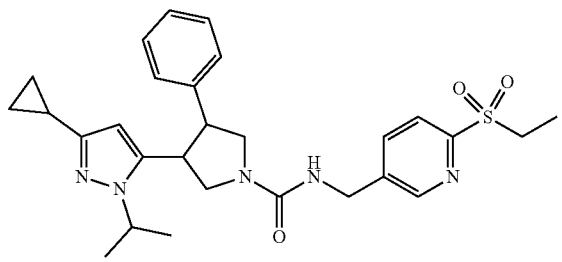
21
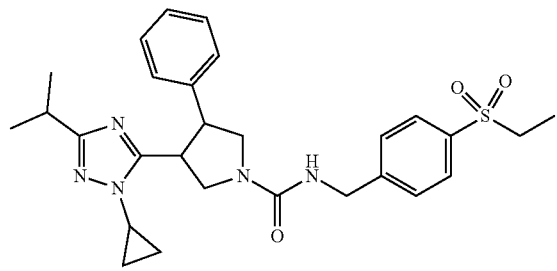
22
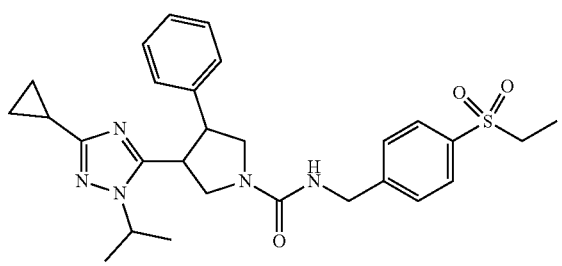
23
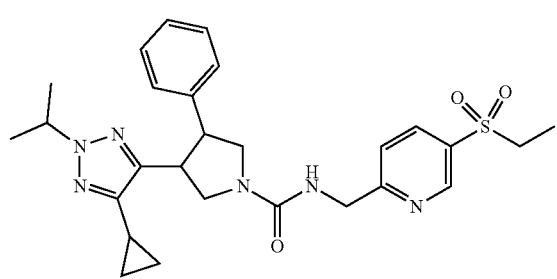
24
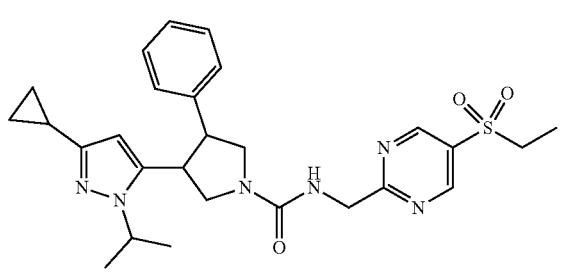

25
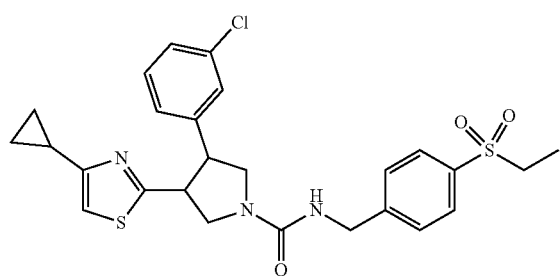
28
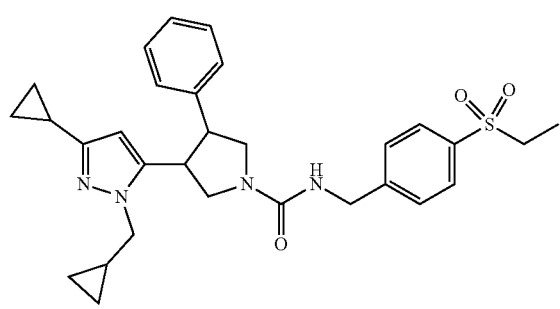
31
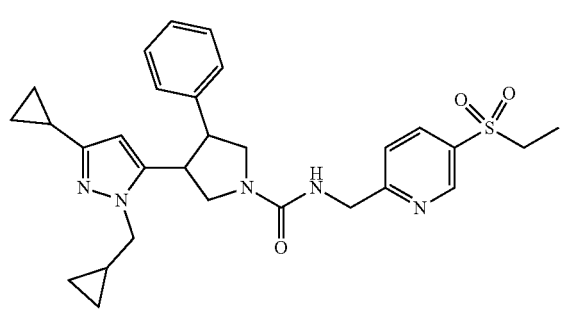
32
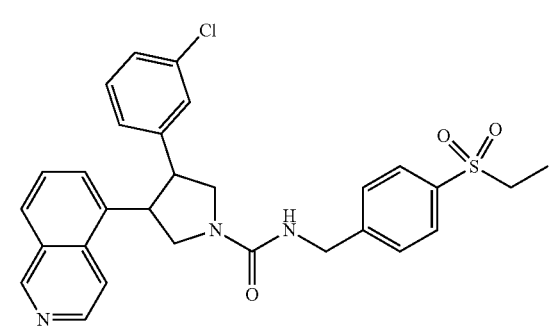
33
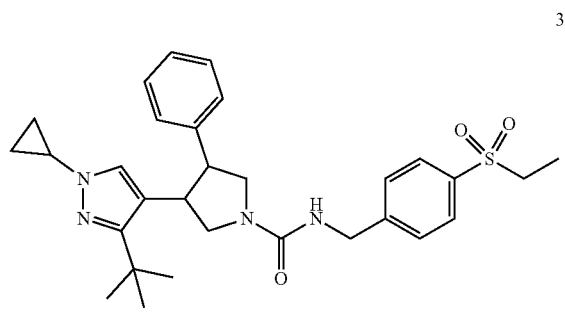
34
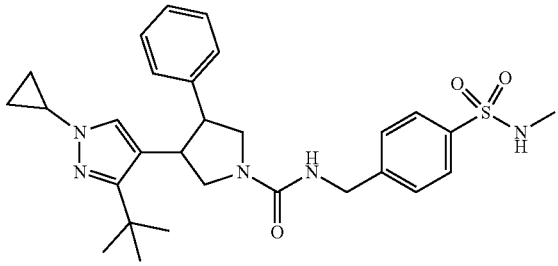
35
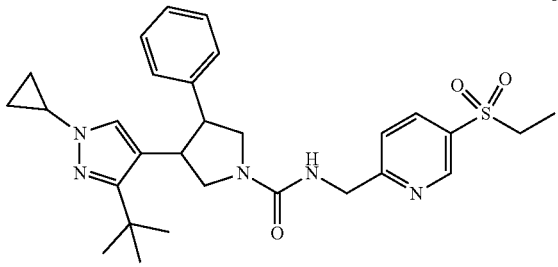
36
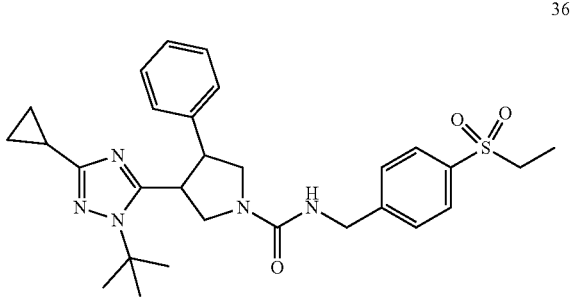
37
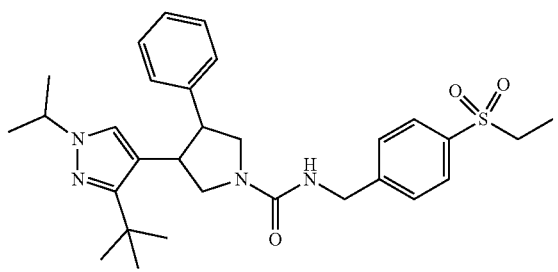
38
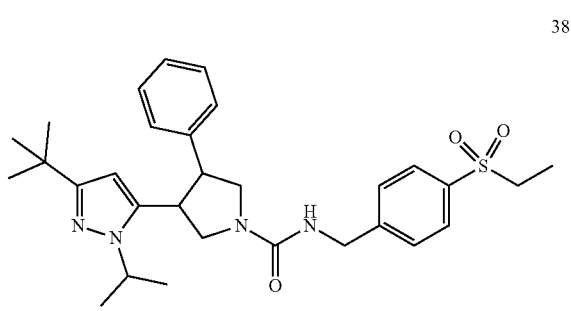

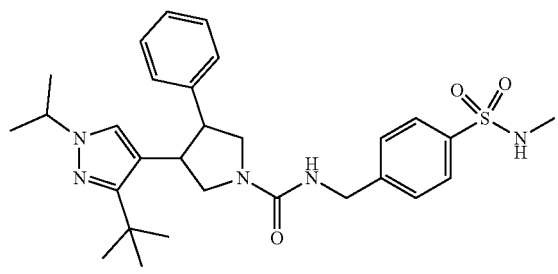
39
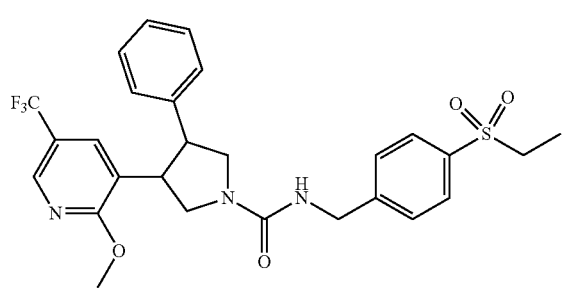
44
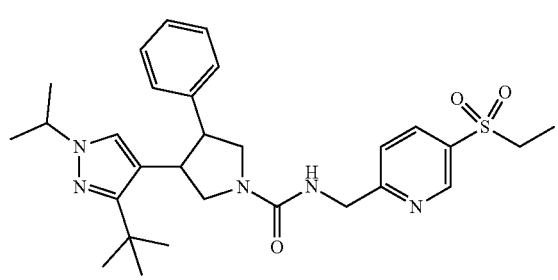
40
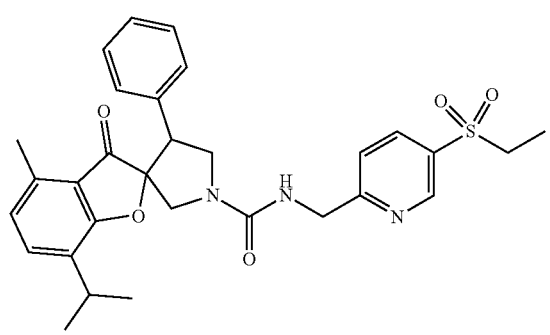
45
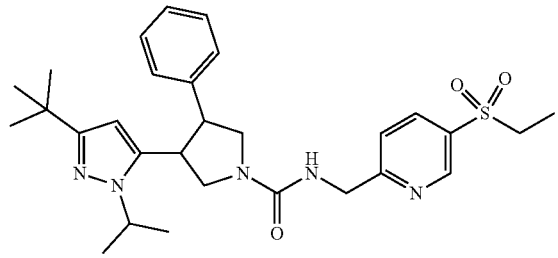
41
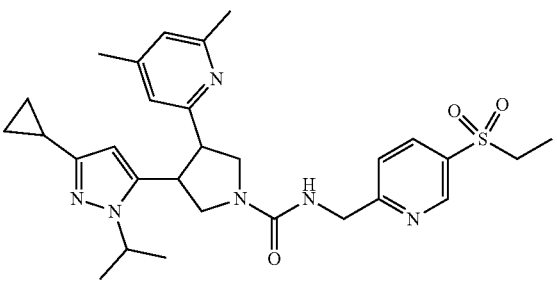
46
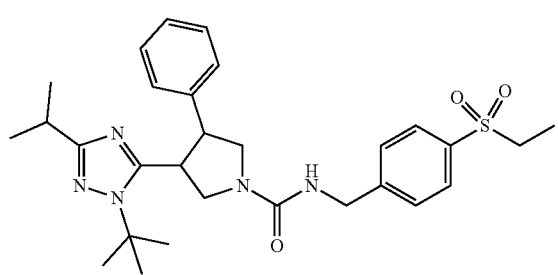
42
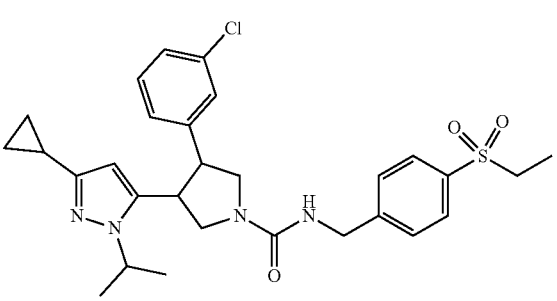
48
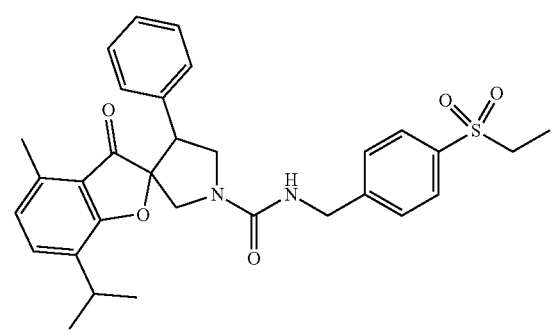
43
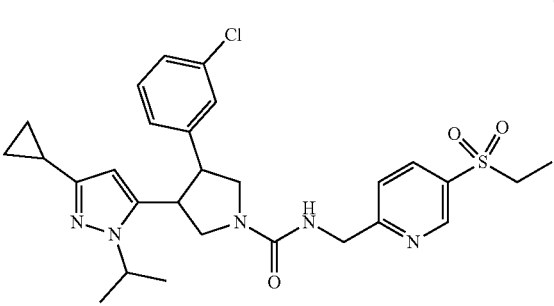
49

50

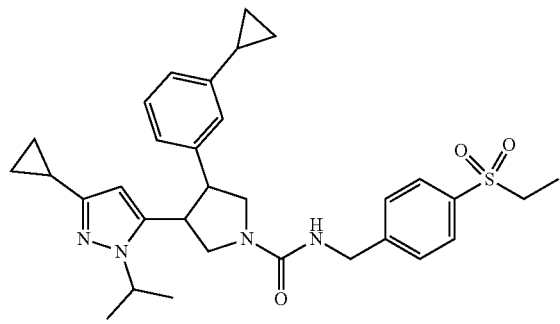

51

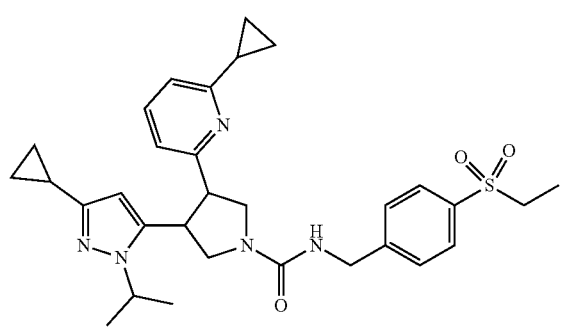

52

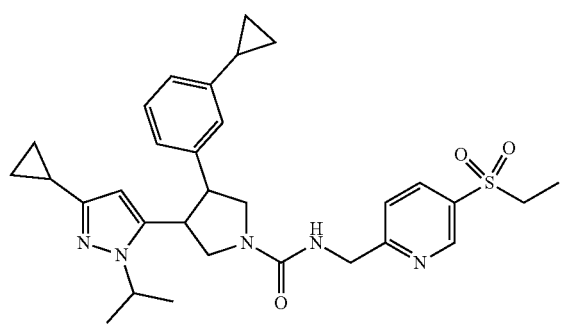

53

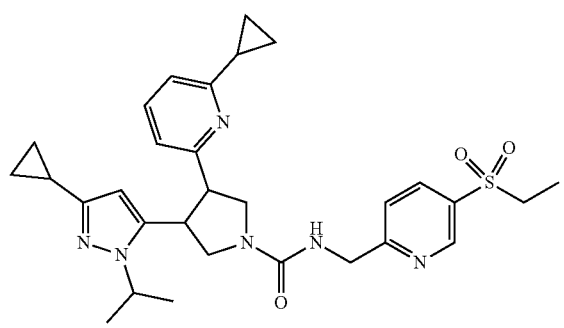

54

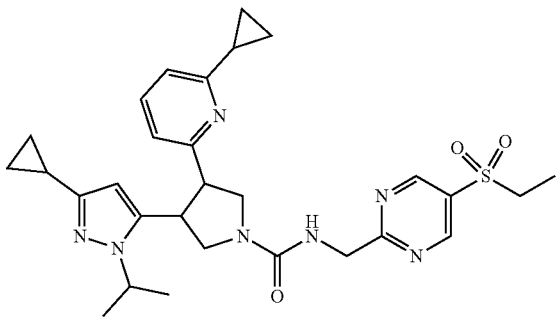

55

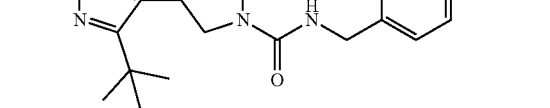

56

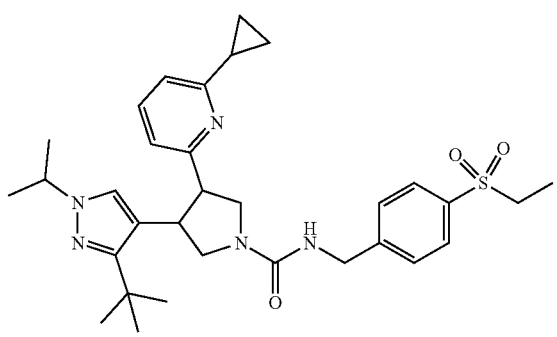

57 the enantiomers thereof and the pharmaceutically acceptable salts thereof.

6. A pharmaceutical composition comprising a compound according to claim 1 and a pharmaceutically acceptable excipient or carrier.

7. A method for treating an autoimmune disease or allergic disorder in a patient comprising administering to said patient a therapeutically effective amount of a compound of formula (I) according to claim 1, or a pharmaceutically acceptable salt thereof.

8. The method according to claim 7, wherein the autoimmune disease or allergic disorder is selected from rheumatoid arthritis, psoriasis, systemic lupus erythromatosis, lupus nephritis, scleroderma, asthma, allergic rhinitis, allergic eczema, multiple sclerosis, juvenile rheumatoid arthritis, juvenile idiopathic arthritis, type I diabetes, inflammatory bowel disease, graft versus host disease, psoriatic arthritis, reactive arthritis, ankylosing spondylitis, Crohn's disease, ulcerative colitis, uveitis and non-radiographic spondyloarthropathy.

* * * * *